United States Patent
Cai et al.

(10) Patent No.: US 7,135,480 B2
(45) Date of Patent: Nov. 14, 2006

(54) SUBSTITUTED 1-BENZOYL-3-CYANO-PYRROLO [1,2-A] QUINOLINES AND ANALOGS AS ACTIVATORS OF CASPASES AND INDUCERS OF APOPTOSIS

(75) Inventors: Sui Xiong Cai, San Diego, CA (US); John A Drewe, Carlsbad, CA (US); Sungchun Jiang, San Diego, CA (US); Shailaja Kasibhatla, San Diego, CA (US); Jared Daniel Kuemmerle, Del Mar, CA (US); Nilantha Sudath Sirisoma, San Diego, CA (US); Han-Zhong Zhang, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 153 days.

(21) Appl. No.: 10/733,229

(22) Filed: Dec. 12, 2003

(65) Prior Publication Data

US 2005/0014759 A1 Jan. 20, 2005

Related U.S. Application Data

(60) Provisional application No. 60/432,608, filed on Dec. 12, 2002.

(51) Int. Cl.
*A61K 31/4745* (2006.01)
*C07D 471/02* (2006.01)
(52) U.S. Cl. .................. 514/294; 546/94; 544/126; 544/361; 514/233.2; 514/253
(58) Field of Classification Search ............... 514/294, 514/233.2, 253; 546/94; 544/126, 361
See application file for complete search history.

(56) References Cited

OTHER PUBLICATIONS

Tewari, R.S. et al.: Studies on 1,3-dipolar cycloaddition reactions of some cycloimmonium Ylides. J. Chem. Eng. Data, vol. 27, pp. 101-103, 1982.*
Tewari, R.S. et al.: Studies on 1,3-dipolar cycloaddition reactions of some cycloimmonium Ylides. J. Chem. Eng. Data, vol. 28, pp. 283-285, 1983.*
Georgescu, E.I. et al.: N-bridged heterocyclic compounds. Revue Roumaine de Chimie, vol. 46, pp. 357-362, 2001.*
Dumitrascu, F., et al., "Primary cycloadducts of 1,10-phenanthrolinium and phthalazinium phenacylides with DMAD," *Tetrahedron Letters* 42:8379-8382, Elsevier Science Ltd (Sep. 2001).

Henrick, C.A., et al., "Pyridinium Ylids In Synthesis," *Aust. J. Chem.* 20:2467-2477, Commonwealth Scientific and Industrial Research Organization (1967).
Irwin, W.J., et al., "Pyrrolo[1,2- a]quinolines. A Re-investigation," *J. Chem. Soc. Perkins I* 2:250-252, The Royal Society of Chemistry (1974).
Kuo, H., et al., "Synthesis and Reaction of 2.7-Dimethylpyrrolo[1,2-a]quinoline with Electrophilic Reagents," *J. Heterocycl. Chem.* 16:393-395, HeteroCorporation (1979).
Matusiak, G., "1,3-Dipolar Cycloaddition Reactions of the Ylide Derived from 6-Phenacyl-benzo[f][1,7]naphthyridinium Bromide," *Aust. J. Chem.* 52:149-151, Commonwealth Scientific and Industrial Research Organization (1999).
Wei, X., et al., "A Facile One-step Synthesis of Aromatic Indolizines by 1,3-Dipolar Cycloaddition of Pyridinium and Related Heteroaromatic Ylides with Alkenes in the Presence of TPCD [Copy$_4$(HCrO$_4$)$_2$]," *J. Chem. Soc. Perkin Trans. 1* 1:2487-2489, The Royal Society of Chemistry (1993).
International Search Report for International Application No. PCT/US03/39550, U.S. Patent and Trademark Office, mailed on Jun. 22, 2004.

* cited by examiner

*Primary Examiner*—Charanjit S. Aulakh
(74) *Attorney, Agent, or Firm*—Sterne, Kessler, Goldstein & Fox P.L.L.C.

(57) ABSTRACT

The present invention is directed to substituted 1-benzoyl-3-cyano-pyrrolo[1,2-α]quinolines and analogs thereof, represented by the general Formula I:

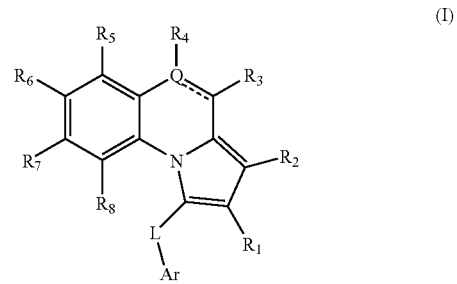

(I)

wherein $R_1$–$R_8$, L, Q, dash line and Ar are defined herein. The present invention also relates to the discovery that compounds having Formula I are activators of caspases and inducers of apoptosis. Therefore, the activators of caspases and inducers of apoptosis of this invention can be used to induce cell death in a variety of clinical conditions in which uncontrolled growth and spread of abnormal cells occurs.

21 Claims, No Drawings

SUBSTITUTED 1-BENZOYL-3-CYANO-PYRROLO [1,2-A] QUINOLINES AND ANALOGS AS ACTIVATORS OF CASPASES AND INDUCERS OF APOPTOSIS

BACKGROUND OF THE INVENTION

1. Field of the Invention

This invention is in the field of medicinal chemistry. In particular, the invention relates to substituted 1-benzoyl-3-cyano-pyrrolo[1,2-a]quinolines and analogs, and the discovery that these compounds are activators of caspases and inducers of apoptosis. The invention also relates to the use of these compounds as therapeutically effective anti-cancer agents.

2. Description of Background Art

Organisms eliminate unwanted cells by a process variously known as regulated cell death, programmed cell death, or apoptosis. Such cell death occurs as a normal aspect of animal development, as well as in tissue homeostasis and aging (Glucksmann, A., Biol. Rev. Cambridge Philos. Soc. 26:59–86 (1951); Glucksmann, A., Archives de Biologie 76:419–437 (1965); Ellis, et al., Dev. 112:591–603 (1991); Vaux, et al., Cell 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane-enclosed particles containing intracellular material) (Orrenius, S., J. Internal Medicine 237:529–536 (1995)).

Apoptosis is achieved through an endogenous mechanism of cellular suicide (Wyllie, A. H., in Cell Death in Biology and Pathology, Bowen and Lockshin, eds., Chapman and Hall, pp. 9–34 (1981)). A cell activates its internally-encoded suicide program as a result of either internal or external signals. The suicide program is executed through the activation of a carefully regulated genetic program (Wyllie, et al., Int. Rev. Cyt. 68:251 (1980); Ellis, et al., Ann. Rev. Cell Bio. 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., J. Internal Medicine 237:529–536 (1995)).

It has been found that a group of proteases are a key element in apoptosis (see, e.g., Thornberry, Chemistry and Biology 5:R97–R103 (1998); Thornberry, British Med. Bull. 53:478–490 (1996)). Genetic studies in the nematode Caenorhabditis elegans revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase 1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (Apoptosis and Cancer Chemotherapy, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide so the cells become immortal—they become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (Schmitt, et al., Biochem. Cell. Biol. 75:301–314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., Blood 90(8):3118–3129 (1997); Friesen, et al., Nat. Med. 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis, occurs in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow-growing tumors, e.g. colon cancers, exist primarily in the $G_o$ phase, whereas rapidly proliferating normal tissues, e.g. bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., Goodman and Gilman's The Pharmacological Basis of Therapeutics, Ninth Edition, McGraw-Hill, New York, pp. 1225–1287 (1996)). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

The synthesis of aromatic indolizines by 1,3-dipolar cycloaddition of pyridinium ylides, quinolinium ylides or isoquinolinium ylide with alkenes was reported by Wei, et al., *J. Chem. Soc. Perkin Trans.* 1:2487–2489 (1993). One of the compound synthesized is 1-benzoyl-3-cyano-pyrrolo[1,2-a]-quinoline.

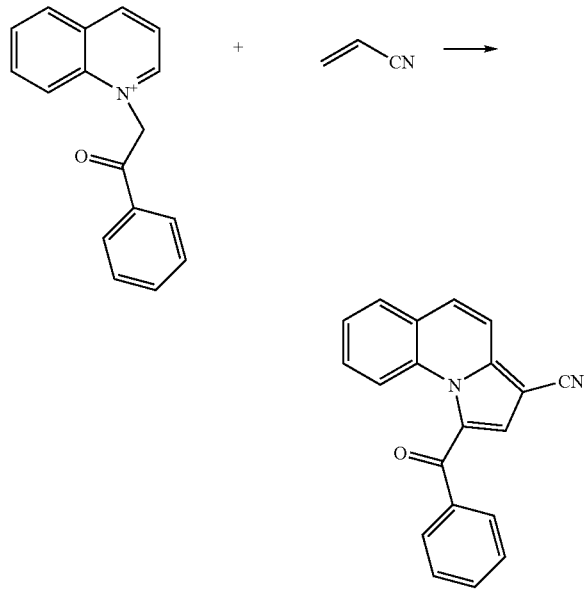

SUMMARY OF THE INVENTION

The present invention is related to the discovery that substituted 1-benzoyl-3-cyano-pyrrolo[1,2-α]quinolines and analogs, as represented in Formulae I–IV, are activators of the caspase cascade and inducers of apoptosis. Therefore, the first aspect of the present invention is directed to the use of compounds of Formulae I–IV as inducers of apoptosis.

A second aspect of the present invention is to provide a method for treating, preventing or ameliorating neoplasia and cancer by administering a compound of Formulae I–IV to a mammal in need of such treatment.

A third aspect of the present invention is to provide novel compounds of Formulae I–IV, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formulae I–IV in admixture with one or more pharmaceutically acceptable carriers or diluents.

A fifth aspect of the present invention is directed to methods for the preparation of novel compounds of Formulae I–IV.

DETAILED DESCRIPTION OF THE INVENTION

The present invention arises out of the discovery that substituted 1-benzoyl-3-cyano-pyrrolo[1,2-a]quinolines and analogs are potent and highly efficaceous activators of the caspase cascade and inducers of apoptosis. Therefore, these compounds are useful for treating disorders responsive to induction of apoptosis.

Specifically, compounds useful in this aspect of the present invention are substituted 1-benzoyl-3-cyano-pyrrolo [1,2-a]quinolines and analogs as represented by Formula I:

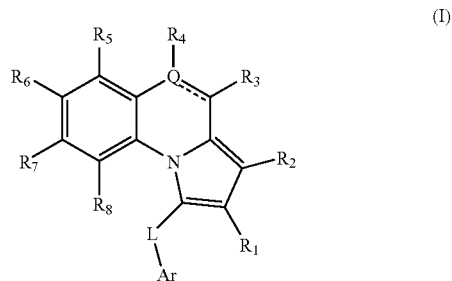

(I)

and pharmaceutically acceptable salts and prodrugs thereof, wherein:

L is C=O or CHOH;

Ar is optionally substituted and is aryl, heteroaryl, saturated carbocyclic, partially saturated carbocylic, saturated heterocyclic, partially saturated heterocyclic, arylalkyl, or heteroarylalkyl;

$R_1$–$R_8$ are independently hydrogen, halo, haloalkyl, aryl, optionally substituted fused aryl, optionally substituted fused heteroaryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol, alkylsulfonyl or alkylcarboxylate;

the dash line represents either a single bond or a double bond; and

Q is N or C, with the proviso that when Q is N and the dash line represents a double bond, then $R_4$ is either O or none.

Preferred compounds falling within the scope of Formula I include compounds wherein $R_1$–$R_8$ are independently hydrogen, halo, haloalkyl, aryl, optionally substituted fused heteroaryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol, alkylsulfonyl or alkylcarboxylate. More preferably, $R_1$–$R_8$ are independently hydrogen, halo, haloalkyl, aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol, alkylsulfonyl or alkylcarboxylate. Most preferably, $R_1$ and $R_3$–$R_8$ are independently hydrogen, methyl, methoxy, nitro or halo.

Preferably, $R_2$ is —C(O)—($C_{1-10}$)alkyl, —C(O)—O—($C_{1-10}$)alkyl or CN. More preferably $R_2$ is CN. Preferably L is C=O. Preferably Ar is phenyl, naphthyl, pyridyl, quinolyl, isoquinolyl, thienyl, furyl, pyrrolyl, indolyl, or cyclohexyl. More preferably Ar is phenyl or pyridyl; most preferably, phenyl. Preferably Q is C. Preferably the dash line is a double bond.

One embodiment of the present invention is directed to compounds of Formula II:

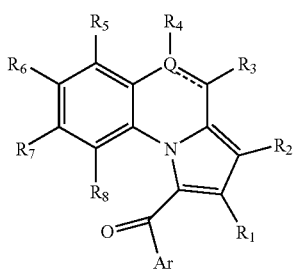

(II)

and pharmaceutically acceptable salts and prodrugs thereof, where $R_1$–$R_8$, Q, dash line and Ar are as defined above.

Preferred compounds falling within the scope of Formula II include compounds wherein $R_1$–$R_8$ are independently hydrogen, halo, haloalkyl, aryl, optionally substituted fused heteroaryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol, alkylsulfonyl or alkylcarboxylate. More preferably, $R_1$–$R_8$ are independently hydrogen, halo, haloalkyl, aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol, alkylsulfonyl or alkylcarboxylate. Most preferably, $R_1$ and $R_3$–$R_8$ are independently hydrogen, methyl, methoxy, nitro or halo.

Preferably, $R_2$ is —C(O)—($C_{1-10}$)alkyl, —C(O)—O—($C_{1-10}$)alkyl or CN. More preferably $R_2$ is CN. Preferably Q is C. Preferably the dash line is a double bond.

Another embodiment of the present invention is directed to compounds of Formula III:

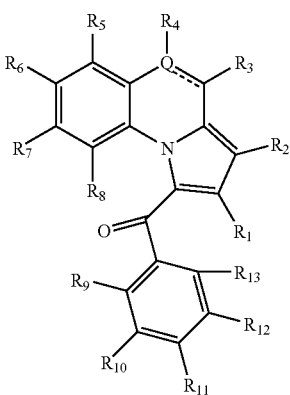

(III)

and pharmaceutically acceptable salts and prodrugs thereof, wherein:

$R_1$–$R_8$, dash line and Q are as defined above; and $R_9$–$R_{13}$ are independently hydrogen, halo, $C_1$–$C_6$ haloalkyl, $C_6$–$C_{10}$ aryl, heteroaryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$) alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy, carboxy, ($C_1$–$C_6$)alkylsulfonyl or ($C_1$–$C_6$)alkylcarboxylate.

Preferably, $R_9$–$R_{13}$ are independently hydrogen, methyl, methoxy, halo, pyridinyl, pyrrolidinyl, amino (including —NH$_2$, diethylamino and 2-morpholin-4-yl-ethylamino), imidazolyl, methylcarboxylate, methanesulfonyl, hydroxyimidazolyl, pyridinylpiperazinyl, morpholinyl or methylpiperazinyl.

Another embodiment of the present invention is directed to compounds of Formula IV:

(IV)

and pharmaceutically acceptable salts and prodrugs thereof, wherein:

$R_1$–$R_6$ and $R_9$–$R_{13}$ are as described above; and $R_{14}$–$R_{16}$ are independently hydrogen, halo, $C_1$–$C_6$ haloalkyl, $C_6$–$C_{10}$ aryl, heteroaryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$) alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy, carboxy, ($C_1$–$C_6$)alkylsulfonyl or ($C_1$–$C_6$)alkylcarboxylate.

Exemplary preferred compounds that may be employed in the method of invention include, without limitation:

1-Benzoyl-3-cyano-pyrrolo[1,2-a]quinoline;
1-(4-Methyl-benzoyl)-3-(1-oxo-ethyl)-pyrrolo[1,2-a]quinoline;
3-(Ethyl carboxylate)-1-(4-methoxy-benzoyl)-pyrrolo[1,2-a]quinoline;
3-(Ethyl carboxylate)-1-(3-methoxy-benzoyl)-pyrrolo[1,2-a]quinoline;
1-Benzoyl-3-(ethylcarboxylate)-11,11c-diaza-cyclopenta[c]-phenan-threne;
3-Cyano-1-(3-methoxy-benzoyl)-pyrrolo[1,2-a]quinoline;
1-(3-Bromo-benzoyl)-3-cyano-pyrrolo[1,2-a]quinoline;
3-Cyano-1-(4-methoxy-benzoyl)-pyrrolo[1,2-a]quinoline;
3-Cyano-1-(4-methyl-benzoyl)-pyrrolo[1,2-a]quinoline;
1-(4-Chloro-benzoyl)-3-cyano-pyrrolo[1,2-a]quinoline;
3-Cyano-1-(4-fluoro-benzoyl)-pyrrolo[1,2-a]quinoline;
1-(4-Bromo-benzoyl)-3-cyano-pyrrolo[1,2-a]quinoline;
1-Benzoyl-3-cyano-7-methyl-pyrrolo[1,2-a]quinoline;
1-Benzoyl-3-cyano-5-methyl-pyrrolo[1,2-a]quinoline;
3-Cyano-1-(4-nitro-benzoyl)-pyrrolo[1,2-a]quinoline;
1-Benzoyl-3-cyano-6,7,8,9-tetrahydro-pyrrolo[1,2-a]quinoline;
3-Cyano-1-(pyridine-2-carbonyl)-pyrrolo[1,2-a]quinoline;

3-Cyano-1-(pyridine-3-carbonyl)-pyrrolo[1,2-a]quinoline;
3-Cyano-1-(4-pyrrolidin-1-yl-benzoyl)-pyrrolo[1,2-a]quinoline;
3-Cyano-1-[hydroxy-(4-methoxyphenyl)-methyl]-pyrrolo[1,2-a]quinoline;
1-(4-Amino-benzoyl)-3-cyano-pyrrolo[1,2-a]quinoline;
3-Cyano-1-(4-imidazol-1-yl-benzoyl)-pyrrolo[1,2-a]quinoline;
3-Cyano-1-cyclopropanecarbonyl-pyrrolo[1,2-a]quinoline;
3-Cyano-1-[4-(methyl carboxylate)benzoyl]-pyrrolo[1,2-a]quinoline;
3-Cyano-1-(4-diethylmino-benzoyl)-pyrrolo[1,2-a]quinoline;
3-Cyano-1-(4-methanesulfonyl-benzoyl)-pyrrolo[1,2-a]quinoline;
3-Cyano-1-[hydroxy-(4-imidazol-1-yl-phenyl)-methyl]-pyrrolo[1,2-a]quinoline;
3-Cyano-1-[imidazol-1-yl-(4-imidazol-1-yl-phenyl)-methyl]-pyrrolo[1,2-a]quinoline;
3-Cyano-1-[4-(4-pyridin-2-yl-piperazin-1-yl)-benzoyl]-pyrrolo[1,2-a]quinoline;
3-Cyano-1-[4-(2-morpholin-4-yl-ethylamino)-benzoyl]-pyrrolo[1,2-a]quinoline;
3-Cyano-1-(4-morpholin-4-yl-benzoyl)-pyrrolo[1,2-a]quinoline;
3-Cyano-1-[4-(4-methyl-piperazin-1-yl)-benzoyl]-pyrrolo[1,2-a]quinoline;
1-Benzoyl-3-cyano-8-methyl-pyrrolo[1,2-a]quinoline;
1-Benzoyl-6-chloro-3-cyano-pyrrolo[1,2-a]quinoline;
1-Benzoyl-4-bromo-3-cyano-pyrrolo[1,2-a]quinoline;
1-Benzoyl-7-chloro-3-cyano-pyrrolo[1,2-a]quinoline;
3-Cyano-1-(morpholine-4-carbonyl)-pyrrolo[1,2-a]quinoline;
3-Cyano-1-(4-pyrazol-1-yl-benzoyl)-pyrrolo[1,2-a]quinoline;
1-Benzoyl-3-cyano-4-methyl-pyrrolo[1,2-a]quinoline;
3-Cyano-1-(4-fluoro-benzoyl)-8-methyl-pyrrolo[1,2-a]quinoline;
3-Cyano-1-(4-imidazol-1-yl-benzoyl)-8-methyl-pyrrolo[1,2-a]quinoline;
3-Cyano-1-(hydroxy-phenyl-methyl)-pyrrolo[1,2-a]quinoline;
3-Cyano-1-[hydroxy-(4-fluorophenyl)-methyl]-pyrrolo[1,2-a]quinoline;
3-Cyano-1-(hydroxy-phenyl-methyl)-8-methyl-pyrrolo[1,2-a]quinoline;
6-Chloro-3-cyano-1-(hydroxy-phenyl-methyl)-pyrrolo[1,2-a]quinoline;
3-Cyano-1-[hydroxy-(4-pyrazol-1-yl-phenyl)-methyl]-pyrrolo[1,2-a]quinoline;
6-Chloro-3-cyano-1-(4-fluoro-benzoyl)-pyrrolo[1,2-a]quinoline;
6-Chloro-3-cyano-1-(4-imidazol-1-yl-benzoyl)-pyrrolo[1,2-a]quinoline;
3-Cyano-1-(4-piperazin-1-yl-benzoyl)-pyrrolo[1,2-a]quinoline;
3-Cyano-1-[4-(3-dimethylamino-propylamino)-benzoyl]-pyrrolo[1,2-a]quinoline;
3-Cyano-1-(4-methoxy-benzoyl)-pyrrolo[1,2-a]quinoxaline;
3-Cyano-4,5-dihydro-1-(4-methoxy-benzoyl)-pyrrolo[1,2-a]quinoxaline;
3-Cyano-1-(3-hydroxy-benzoyl)-pyrrolo[1,2-a]quinoline;
3-Cyano-1-[3-(2-morpholin-4-yl-ethoxy)benzoyl]-pyrrolo[1,2-a]quinoline;
3-Cyano-1-[3-(2-dimethylamino-ethoxy)benzoyl]-pyrrolo[1,2-a]quinoline;
3-Cyano-1-[3-(carboxymethoxy)benzoyl]-pyrrolo[1,2-a]quinoline;
3-Cyano-1-[3-(2-hydroxyethoxy)benzoyl]-pyrrolo[1,2-a]quinoline;
3-Cyano-1-[2-(dimethylaminomethyl)benzoyl]-pyrrolo[1,2-a]quinoline;
3-Cyano-1-[4-(dimethylaminomethyl)benzoyl]-pyrrolo[1,2-a]quinoline;
3-Cyano-1-[4-(morpholin-4-ylmethyl)benzoyl]-pyrrolo[1,2-a]quinoline;
3-Cyano-1-[4-(4-methylpiperazin-1-ylmethyl)benzoyl]-pyrrolo[1,2-a]quinoline;
3-Cyano-1-[4-(imidazol-1-ylmethyl)benzoyl]-pyrrolo[1,2-a]quinoline;
3-Cyano-1-(4-fluoro-benzoyl)-8-dimethylaminomethyl-pyrrolo[1,2-a]quinoline;
3-Cyano-1-(4-dimethylamino-benzoyl)-pyrrolo[1,2-a]quinoline;
1-Benzoyl-3-cyano-6-nitro-pyrrolo[1,2-a]quinoline;
1-Benzoyl-3-cyano-6-hydroxy-pyrrolo[1,2-a]quinoline;
1-Benzoyl-3-cyano-8-hydroxy-pyrrolo[1,2-a]quinoline;
1-Benzoyl-3-cyano-6-(2-morpholin-4-yl-ethoxy)-pyrrolo[1,2-a]quinoline;
1-Benzoyl-3-cyano-6-(2-dimethylamino-ethoxy)-pyrrolo[1,2-a]quinoline;
1-Benzoyl-3-cyano-8-(2-morpholin-4-yl-ethoxy)-pyrrolo[1,2-a]quinoline;
1-Benzoyl-3-cyano-8-(2-dimethylamino-ethoxy)-pyrrolo[1,2-a]quinoline;
1-(3-Methoxy-benzoyl)-pyrrolo[1,2-a]quinoline-3-carboxylic acid;
1-(3-Methoxy-benzoyl)-pyrrolo[1,2-a]quinoline-3-carboxylic acid N-hydroxysuccinimidyl ester;
1-(3-Methoxy-benzoyl)-pyrrolo[1,2-a]quinoline-3-carboxylic acid (2-hydroxy-ethyl)-amide;
1-(3-Methoxy-benzoyl)-pyrrolo[1,2-a]quinoline-3-carboxylic acid (2-morpholin-4-yl-ethyl)-amide;
1-(3-Methoxy-benzoyl)-pyrrolo[1,2-a]quinoline-3-carboxylic acid hydroxy-amide;
1-(3-Methoxy-benzoyl)-pyrrolo[1,2-a]quinoline-3-carboxylic acid (2-amino-ethyl)-amide;
1-(3-Methoxy-benzoyl)-pyrrolo[1,2-a]quinoline-3-carboxylic acid (3-dimethylamino-propyl)-amide;
1-(3-Methoxy-benzoyl)-pyrrolo[1,2-a]quinoline-3-carboxylic acid {2-[2-(2-amino-ethoxy)-ethoxy-]-ethyl}-amide;
1-(3-Methoxy-benzoyl)-3-(4-methyl-piperazine-1-cabonyl)-pyrrolo[1,2-a]quinoline;
1-(3-Methoxy-benzoyl)-pyrrolo[1,2-a]quinoline-3-carboxylic acid (2-piperazin-1-yl-ethyl)-amide;
3-Cyano-1-(2-fluoro-benzoyl)-pyrrolo[1,2-a]quinoline;
3-Cyano-1-(2-methylbenzoyl)-pyrrolo[1,2-a]quinoline;
3-Cyano-1-(4-acetamido-3-nitro-benzoyl)-pyrrolo[1,2-a]quinoline;
3-Cyano-1-(4-fluoro-benzoyl)-pyrrolo[1,2-a]quinoxaline;
3-Cyano-1-(2-imidazol-1-yl-benzoyl)-pyrrolo[1,2-a]quinoline;
3-Cyano-1-(2-morpholine-1-yl-benzoyl)-pyrrolo[1,2-a]quinoline; and
3-Cyano-1-(4-carboxy-benzoyl)-pyrrolo[1,2-a]quinoline.

The present invention is also directed to novel compounds within the scope of Formulae I–IV. Exemplary preferred compounds that may be employed in this invention include, without limitation:
3-Cyano-1-(3-methoxy-benzoyl)-pyrrolo[1,2-a]quinoline;
1-(3-Bromo-benzoyl)-3-cyano-pyrrolo[1,2-a]quinoline;
3-Cyano-1-(4-methoxy-benzoyl)-pyrrolo[1,2-a]quinoline;
3-Cyano-1-(4-methyl-benzoyl)-pyrrolo[1,2-a]quinoline;

1-(4-Chloro-benzoyl)-3-cyano-pyrrolo[1,2-a]quinoline;
3-Cyano-1-(4-fluoro-benzoyl)-pyrrolo[1,2-a]quinoline;
1-(4-Bromo-benzoyl)-3-cyano-pyrrolo[1,2-a]quinoline;
1-Benzoyl-3-cyano-7-methyl-pyrrolo[1,2-a]quinoline;
1-Benzoyl-3-cyano-5-methyl-pyrrolo[1,2-a]quinoline;
3-Cyano-1-(4-nitro-benzoyl)-pyrrolo[1,2-a]quinoline;
1-Benzoyl-3-cyano-6,7,8,9-tetrahydro-pyrrolo[1,2-a]quinoline;
3-Cyano-1-(pyridine-2-carbonyl)-pyrrolo[1,2-a]quinoline;
3-Cyano-1-(pyridine-3-carbonyl)-pyrrolo[1,2-a]quinoline;
3-Cyano-1-(4-pyrrolidin-1-yl-benzoyl)-pyrrolo[1,2-a]quinoline;
3-Cyano-1-[hydroxy-(4-methoxyphenyl)-methyl]-pyrrolo[1,2-a]quinoline;
1-(4-Amino-benzoyl)-3-cyano-pyrrolo[1,2-a]quinoline;
3-Cyano-1-(4-imidazol-1-yl-benzoyl)-pyrrolo[1,2-a]quinoline;
3-Cyano-1-cyclopropanecarbonyl-pyrrolo[1,2-a]quinoline;
3-Cyano-1-[4-(methyl carboxylate)benzoyl]-pyrrol[1,2-a]quinoline;
3-Cyano-1-(4-diethylmino-benzoyl)-pyrrolo[1,2-a]quinoline;
3-Cyano-1-(4-methanesulfonyl-benzoyl)-pyrrolo[1,2-a]quinoline;
3-Cyano-1-[hydroxy-(4-imidazol-1-yl-phenyl)-methyl]-pyrrolo[1,2-a]quinoline;
3-Cyano-1-[imidazol-1-yl-(4-imidazol-1-yl-phenyl)-methyl]-pyrrolo[1,2-a]quinoline;
3-Cyano-1-[4-(4-pyridin-2-yl-piperazin-1-yl)-benzoyl]-pyrrolo[1,2-a]quinoline;
1-[4-(2-Morpholin-4-yl-ethylamino)-benzoyl]-3-cyano-pyrrolo[1,2-a]quinoline;
3-Cyano-1-(4-morpholin-4-yl-benzoyl)-pyrrolo[1,2-a]quinoline;
3-Cyano-1-[4-(4-methyl-piperazin-1-yl)-benzoyl]-pyrrolo[1,2-a]quinoline;
1-Benzoyl-3-cyano-8-methyl-pyrrolo[1,2-a]quinoline;
1-Benzoyl-6-chloro-3-cyano-pyrrolo[1,2-a]quinoline;
1-Benzoyl-4-bromo-3-cyano-pyrrolo[1,2-a]quinoline;
1-Benzoyl-7-chloro-3-cyano-pyrrolo[1,2-a]quinoline;
3-Cyano-1-(morpholine-4-carbonyl)-pyrrolo[1,2-a]quinoline;
3-Cyano-1-(4-pyrazol-1-yl-benzoyl)-pyrrolo[1,2-a]quinoline;
1-Benzoyl-3-cyano-4-methyl-pyrrolo[1,2-a]quinoline;
3-Cyano-1-(4-fluoro-benzoyl)-8-methyl-pyrrolo[1,2-a]quinoline;
3-Cyano-1-(4-imidazol-1-yl-benzoyl)-8-methyl-pyrrolo[1,2-a]quinoline;
3-Cyano-1-(hydroxy-phenyl-methyl)-pyrrolo[1,2-a]quinoline;
3-Cyano-1-[hydroxy-(4-fluorophenyl)-methyl]-pyrrolo[1,2-a]quinoline;
3-Cyano-1-(hydroxy-phenyl-methyl)-8-methyl-pyrrolo[1,2-a]quinoline;
6-Chloro-3-cyano-1-(hydroxy-phenyl-methyl)-pyrrolo[1,2-a]quinoline;
3-Cyano-1-[hydroxy-(4-pyrazol-1-yl-phenyl)-methyl]-pyrrolo[1,2-a]quinoline;
6-Chloro-3-cyano-1-(4-fluoro-benzoyl)-pyrrolo[1,2-a]quinoline;
6-Chloro-3-cyano-1-(4-imidazol-1-yl-benzoyl)-pyrrolo[1,2-a]quinoline;
3-Cyano-1-(4-piperazin-1-yl-benzoyl)-pyrrolo[1,2-a]quinoline;
3-Cyano-1-[4-(3-dimethylamino-propylamino)-benzoyl]-pyrrolo[1,2-a]quinoline;
3-Cyano-1-(4-methoxy-benzoyl)-pyrrolo[1,2-a]quinoxaline;
3-Cyano-4,5-dihydro-1-(4-methoxy-benzoyl)-pyrrolo[1,2-a]quinoxaline;
3-Cyano-1-(3-hydroxy-benzoyl)-pyrrolo[1,2-a]quinoline;
3-Cyano-1-[3-(2-morpholin-4-yl-ethoxy)benzoyl]-pyrrolo[1,2-a]quinoline;
3-Cyano-1-[3-(2-dimethylamino-ethoxy)benzoyl]-pyrrolo[1,2-a]quinoline;
3-Cyano-1-[3-(carboxymethoxy)benzoyl]-pyrrolo[1,2-a]quinoline;
3-Cyano-1-[3-(2-hydroxyethoxy)benzoyl]-pyrrolo[1,2-a]quinoline;
3-Cyano-1-[2-(dimethylaminomethyl)benzoyl]-pyrrolo[1,2-a]quinoline;
3-Cyano-1-[4-(dimethylaminomethyl)benzoyl]-pyrrolo[1,2-a]quinoline;
3-Cyano-1-[4-(morpholin-4-ylmethyl)benzoyl]-pyrrolo[1,2-a]quinoline;
3-Cyano-1-[4-(4-methylpiperazin-1-ylmethyl)benzoyl]-pyrrolo[1,2-a]quinoline;
3-Cyano-1-[4-(imidazol-1-ylmethyl)benzoyl]-pyrrolo[1,2-a]quinoline;
3-Cyano-1-(4-fluoro-benzoyl)-8-dimethylaminomethyl-pyrrolo[1,2-a]quinoline;
3-Cyano-1-(4-dimethylamino-benzoyl)-pyrrolo[1,2-a]quinoline;
1-Benzoyl-3-cyano-6-nitro-pyrrolo[1,2-a]quinoline;
1-Benzoyl-3-cyano-6-hydroxy-pyrrolo[1,2-a]quinoline;
1-Benzoyl-3-cyano-8-hydroxy-pyrrolo[1,2-a]quinoline;
1-Benzoyl-3-cyano-6-(2-morpholin-4-yl-ethoxy)-pyrrolo[1,2-a]quinoline;
1-Benzoyl-3-cyano-6-(2-dimethylamino-ethoxy)-pyrrolo[1,2-a]quinoline;
1-Benzoyl-3-cyano-8-(2-morpholin-4-yl-ethoxy)-pyrrolo[1,2-a]quinoline;
1-Benzoyl-3-cyano-8-(2-dimethylamino-ethoxy)-pyrrolo[1,2-a]quinoline;
1-(3-Methoxy-benzoyl)-pyrrolo[1,2-a]quinoline-3-carboxylic acid;
1-(3-Methoxy-benzoyl)-pyrrolo[1,2-a]quinoline-3-carboxylic acid N-hydroxysuccinimidyl ester;
1-(3-Methoxy-benzoyl)-pyrrolo[1,2-a]quinoline-3-carboxylic acid (2-hydroxy-ethyl)-amide;
1-(3-Methoxy-benzoyl)-pyrrolo[1,2-a]quinoline-3-carboxylic acid (2-morpholin-4-yl-ethyl)-amide;
1-(3-Methoxy-benzoyl)-pyrrolo[1,2-a]quinoline-3-carboxylic acid hydroxy-amide;
1-(3-Methoxy-benzoyl)-pyrrolo[1,2-a]quinoline-3-carboxylic acid (2-amino-ethyl)-amide;
1-(3-Methoxy-benzoyl)-pyrrolo[1,2-a]quinoline-3-carboxylic acid (3-dimethylamino-propyl)-amide;
1-(3-Methoxy-benzoyl)-pyrrolo[1,2-a]quinoline-3-carboxylic acid {2-[2-(2-amino-ethoxy)-ethoxy-]-ethyl}-amide;
1-(3-Methoxy-benzoyl)-3-(4-methyl-piperazine-1-cabonyl)-pyrrolo[1,2-a]quinoline;
1-(3-Methoxy-benzoyl)-pyrrolo[1,2-a]quinoline-3-carboxylic acid (2-piperazin-1-yl-ethyl)-amide;
3-Cyano-1-(2-fluoro-benzoyl)-pyrrolo[1,2-a]quinoline;
3-Cyano-1-(2-methylbenzoyl)-pyrrolo[1,2-a]quinoline;
3-Cyano-1-(4-acetamido-3-nitro-benzoyl)-pyrrolo[1,2-a]quinoline;
3-Cyano-1-(4-fluoro-benzoyl)-pyrrolo[1,2-a]quinoxaline;
3-Cyano-1-(2-imidazol-1-yl-benzoyl)-pyrrolo[1,2-a]quinoline;
3-Cyano-1-(2-morpholine-1-yl-benzoyl)-pyrrolo[1,2-a]quinoline; and
3-Cyano-1-(4-carboxy-benzoyl)-pyrrolo[1,2-a]quinoline.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkoxy groups include oxygen substituted by one of the $C_{1-10}$ alkyl groups mentioned above, which can be optionally substituted.

Useful alkylthio groups include sulphur substituted by one of the $C_{1-10}$ alkyl groups mentioned above, which can be optionally substituted. Also included are the sulfoxides and sulfones of such alkylthio groups.

Useful amino groups include $-NH_2$, $-NHR_{11}$, and $-NR_{11}R_{12}$, wherein $R_{11}$ and $R_{12}$ are $C_{1-10}$ alkyl or cycloalkyl groups, aryl or heteroaryl groups, or arylalkyl or heteroarylalkyl groups, or $R_{11}$ and $R_{12}$ are combined with the N to form a cycloamino structure, such as a piperidine, or $R_{11}$ and $R_{12}$ are combined with the N and other groups to form a cycloamino structure, such as a piperazine. The alkyl, cycloalkyl, aryl, heteroaryl, cycloamino groups can be optionally substituted.

Optional substituents on the alkyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl($C_2$–$C_6$)alkynyl, saturated and unsaturated heterocyclic, or heteroaryl. Optional substituents on the aryl, aralkyl and heteroaryl groups include one or more halo, $C_1$–$C_6$ haloalkyl, $C_6$–$C_{10}$ aryl, heteroaryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy, carboxy, $(C_1$–$C_6)$alkylsulfonyl and $(C_1$–$C_6)$alkylcarboxylate.

Useful aryl groups are $C_{6-14}$ aryl, especially $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino groups are any $C_{1-6}$ acyl (alkanoyl) attached to an amino nitrogen, e.g., acetamido (acetylamino), propionamido, butanoylamido, pentanoylamido, hexanoylamido, as well as aryl-substituted $C_{2-6}$ substituted acyl groups.

Useful acyloxy groups are any $C_{1-6}$ acyl (alkanoyl) attached to an oxy (—O—) group, e.g., formyloxy, acetoxy, propionoyloxy, butanoyloxy, pentanoyloxy, hexanoyloxy and the like.

Useful saturated or partially saturated heterocyclic groups include tetrahydrofuranyl, pyranyl, piperidinyl, piperazinyl, 4-methyl-piperazinyl, 4-pyridyl-piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include any one of the following: thienyl, benzo[b]thienyl, naphtho[2,3-b]thienyl, thianthrenyl, furanyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]-pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Certain of the compounds of the present invention may exist as stereoisomers including optical isomers. The invention includes all stereoisomers and both the racemic mixtures of such stereoisomers, as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g. those obtained by condensation with a $C_{1-4}$ alcohol according to methods known in the art); esters of hydroxy containing compounds (e.g. those obtained by condensation with a $C_{1-4}$ carboxylic acid, $C_{3-6}$ dioic acid or anhydride thereof (e.g. succinic and fumaric anhydrides according to methods known in the art); imines of amino containing compounds (e.g. those obtained by condensation with a $C_{1-4}$ aldehyde or ketone according to methods known in the art); and acetals and ketals of alcohol containing compounds (e.g. those obtained by condensation with chloromethyl methyl ether or chloromethyl ethyl ether according to methods known in the art).

The compounds of this invention may be prepared using methods known to those skilled in the art, or the novel methods of this invention. Specifically, compounds with Formulae I–IV can be prepared as illustrated by exemplary reactions in Scheme 1. Reaction of a substituted 2-bromoacetylphenone, such as bromo-1-(4-pyrrolidin-1-yl-phenyl)-ethanone with quinoline in a solvent, such as acetonitrile, produced 1-(4-pyrrolidin-1-yl-phenacyl)-quinolinium bromide. Cyclization of the 1-(4-pyrrolidin-1-yl-phenacyl)-quinolinium bromide with an alkene, such as acrylonitrile in the presence of an oxidant, such as tetrapyridinecobalt(II) dichromate (TPCD, Co(II)Py$_4$(HCrO$_4$)$_2$) and a base, such as sodium bicarbonate in a solvent, such as N,N-dimethylformamide (DMF) produced 3-cyano-1-(4-pyrrolidin-1-yl-benzoyl)-pyrrolo[1,2-a]quinoline as the product.

Scheme 1

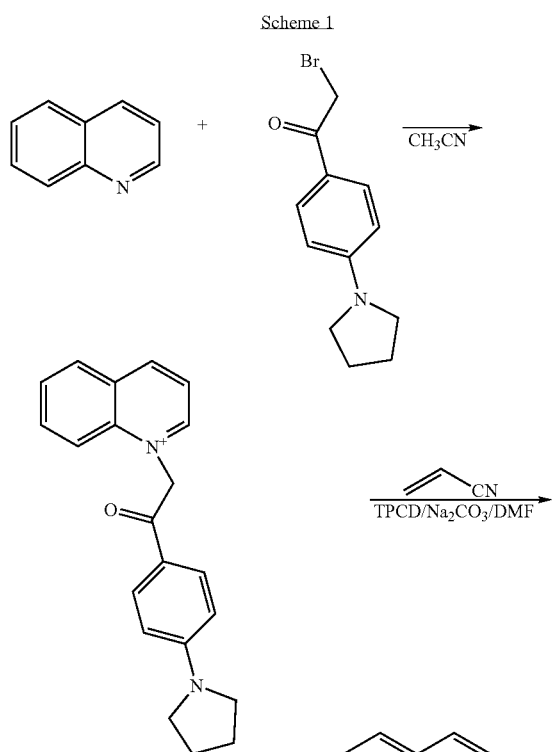

Compound with substitution in the 1-benzoyl group also can be prepared as shown in Scheme 2. 3-cyano-1-(4-fluoro-benzoyl)-pyrrolo[1,2-a]-quinoline was prepared similarly to that described in Scheme 1 from bromo-1-(4-fluoro-phenyl)-ethanone with quinoline, followed by cyclization with acrylonitrile. Reaction of 3-cyano-1-(4-fluoro-benzoyl)-pyrrolo[1,2-a]-quinoline with a nucleophile, such as imidazole, produced the imidazole substituted product.

Scheme 2

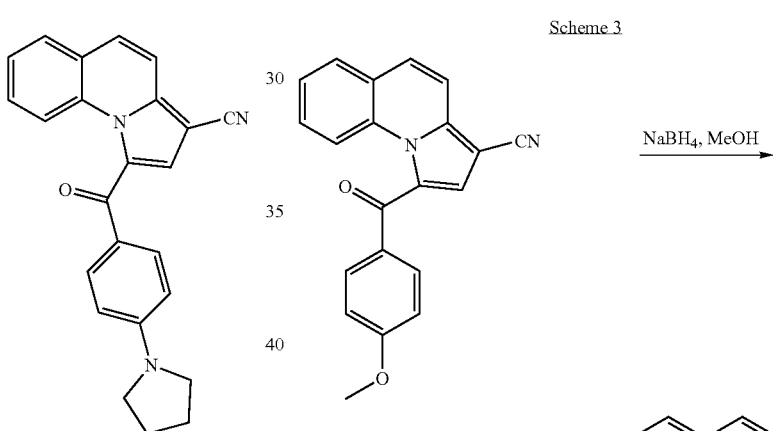

-continued

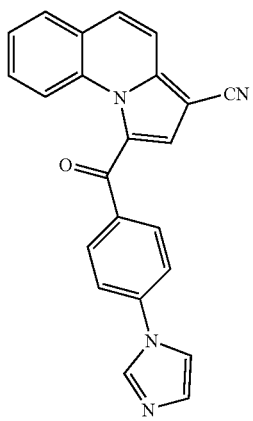

Compound of formula I wherein L is CHOH can be prepared by reduction of the corresponding benzoyl compound. For example, reduction of 3-cyano-1-(4-methoxy-benzoyl)-pyrrolo[1,2-a]quinoline by a reducing agent such as $NaBH_4$ in a solvent such as MeOH produced the hydroxy compound, as shown in Scheme 3.

Scheme 3

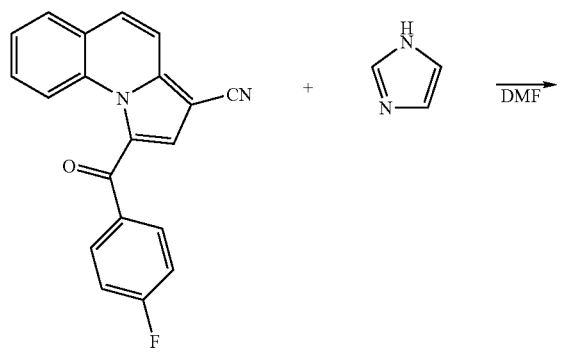

Compound of formula I wherein Q is N can be prepared as illustrated by exemplary reactions in Scheme 4. Reaction of a substituted 2-bromo-acetylphenone, such as bromo-1-(4-methoxy-phenyl)-ethanone with quinoxaline, produced 1-(4-methoxy-phenacyl)-quinolinium bromide. Cyclization of the 1-(4-methoxy-phenacyl)-quinolinium bromide with an alkene, such as acrylonitrile in the presence of an oxidant, such as $MnO_2$ and a base, such as $Et_3N$ in a solvent, such as N,N-dimethylformamide (DMF) produced 3-cyano-1-(4- methoxy-benzoyl)-pyrrolo[1,2-a]quinoxaline as the product. Reduction of 3-cyano-1-(4-methoxy-benzoyl)-pyrrolo[1,2-a]quinoxaline by hydrogenation or NaCNBH$_3$ in MeOH produced 3-cyano-4,5-dihydro-1-(4-methoxy-benzoyl)-pyrrolo[1,2-a]quinoxaline.

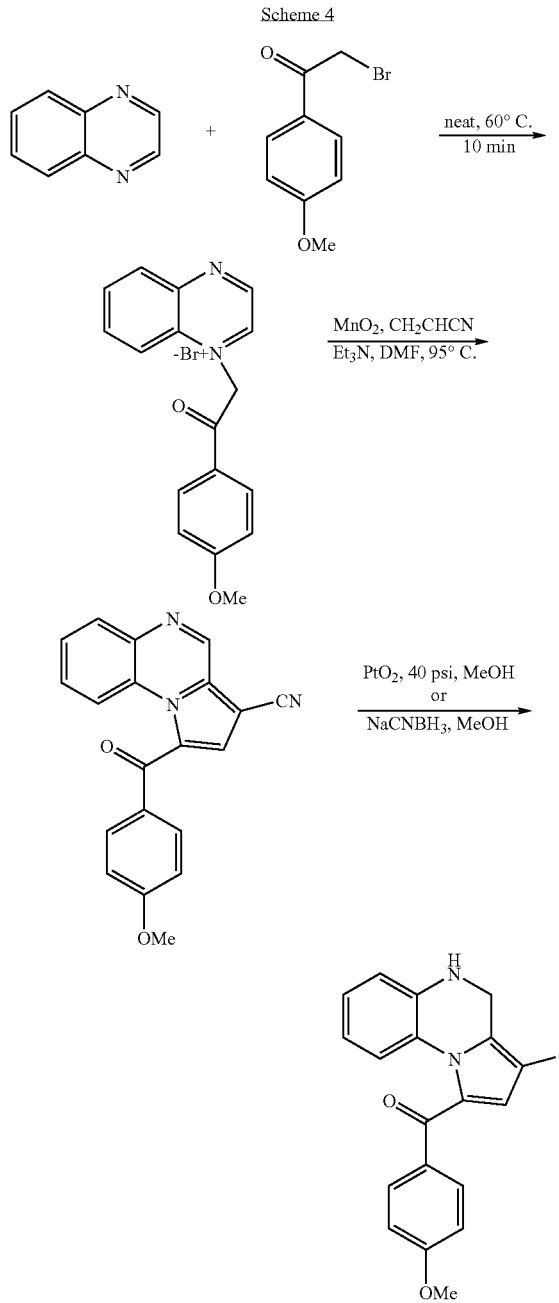

An important aspect of the present invention is the discovery that compounds having Formulae I–IV are activators of caspases and inducers of apoptosis. Therefore, these compounds are useful in a variety of clinical conditions in which there is uncontrolled cell growth and spread of abnormal cells, such as in the case of cancer.

Yet another important aspect of the present invention is the discovery that the compounds described herein are potent and highly efficacious activators of caspases and inducers of apoptosis in drug-resistant cancer cells, such as breast and prostate cancer cells, which enables these compounds to kill drug-resistant cancer cells. In comparison, most standard anti-cancer drugs are not effective in killing drug-resistant cancer cells under the same conditions. Therefore, compounds having Formulae I–IV are expected to be useful for the treatment of drug-resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of a compound described herein, which functions as a caspase cascade activator and inducer of apoptosis.

The present invention also includes a therapeutic method comprising administering to an animal an effective amount of a compound, or a pharmaceutically acceptable salt or prodrug of said compound of Formulae I–IV, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application (for the treatment of neoplastic diseases and other diseases in which caspase cascade mediated physiological responses are implicated), are administered to an individual exhibiting the symptoms of one or more of these disorders. The amounts are effective to ameliorate or eliminate one or more symptoms of the disorder. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

In another embodiment, a pharmaceutical composition comprising a compound, or a pharmaceutically acceptable salt of a compound described herein, which functions as a caspase cascade activator and inducer of apoptosis in combination with a pharmaceutically acceptable vehicle, is provided.

Another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cancer chemotherapeutic agent, or a pharmaceutically acceptable salt of said agent. Examples of known anti-cancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with the at least one known chemotherapeutic agent as part of a unitary pharmaceutical composition. Alternatively, the compound of the invention may be administered apart from the at least one known cancer chemotherapeutic agent. In this embodiment, the compound of the invention and the at least one known cancer chemotherapeutic agent are administered substantially simultaneously, i.e., the compounds are administered at the same time or one after the other, so long as the compounds reach therapeutic levels for a period of time in the blood.

It has been reported that alpha-1-adrenoceptor antagonists, such as doxazosin, terazosin, and tamsulosin, can inhibit the growth of prostate cancer cell via induction of apoptosis (Kyprianou, N., et al., Cancer Res. 60:4550–4555 (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known alpha-1-adrenoceptor antagonists, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., Cancer Res. 55: 408–413 (1995)) and that sigma-2 receptor agonists, such as CB-64D, CB-184 and haloperidol activate a novel apoptotic pathway and potentiate antineoplastic drugs in breast tumor cell lines (Kyprianou, N., et al., Cancer Res. 62:313–322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known sigma-2 receptor agonists, or a pharmaceutically acceptable salt of said agent. Examples of known sigma-2 receptor agonists, which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., Int. J. Cancer 97:746–750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., Nat. Med. 8:225–232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., Cancer Chemother. Pharmacol. 43:145–150 (1999)). 4HPR also was reported to have good activity in combination with gamma-radiation on bladder cancer cell lines (Zou, C., et al., Int. J. Oncol. 13:1037–1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433–443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as STI571 (Imatinib mesilate, Gleevec®), have potent synergetic effect in combination with other anti-leukemic agents, such as etoposide (Liu, W. M., et al., *Br. J. Cancer* 86:1472–1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known tyrosine kinase inhibitor, or a pharmaceutically acceptable salt of said agent. Examples of known tyrosine kinase inhibitors, which can be used for combination therapy include, but are not limited to, Gleevec®, ZD1839. (Iressa), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544–3550 (2001)). Synergy of the protein farnesyltransferase inhibitor SCH66336 and cisplatin in human cancer cell lines also has been reported (Adjei, A. A., et al., *Clin. Cancer. Res.* 7:1438–1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778,123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209–4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cyclin-dependent kinase inhibitor, or a pharmaceutically acceptable salt of said agent. Examples of known cyclin-dependent kinase inhibitor, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology (Huntingt)* 16 (4:3):17–21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known COX-2 inhibitor, or a pharmaceutically acceptable salt of said agent. Examples of known COX-2 inhibitors, which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S., et al., Cell Death Differ. 6(1):13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation (Infante, A. J., et al., J. Pediatr. 133(5):629–633 (1998) and Vaishnaw, A. K., et al., J. Clin. Invest. 103(3):355–363 (1999)). It was reported that overexpression of Bcl-2, which is a member of the Bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., Int. J. Mol. Med. 1(2):475–483 (1998)). Therefore, it is evident that many types of autoimmune disease are caused by defects of the apoptotic process and one treatment strategy would be to turn on apoptosis in the lymphocytes that are causing autoimmune disease (O'Reilly, L. A. and Strasser, A., *Inflamm. Res.* 48(1):5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., J. Immunol. 162(1):603–608 (1999), reported that by direct injection of DNA expression vectors encoding FasL into the inflamed thyroid, the development of lymphocytic infiltration of the thyroid was inhibited and induction of the death of infiltrating T cells was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolyl-maleimide VIII. Potentiation of Fas-mediated apoptosis by bisindolylmaleimide VIII was reported to be selective for activated, rather than non-activated, T cells, and was Fas-dependent. Zhou, T., et al., *Nat. Med.* 5(1):42–8 (1999), reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of a compound described herein, which functions as a caspase cascade activator and inducer of apoptosis, should be an effective treatment for autoimmune disease.

Psoriasis is a chronic skin disease, which is characterized by scaly red patches. Psoralen plus ultraviolet A (PUVA) is a widely-used and effective treatment for psoriasis vulgaris. Coven, T. R., et al., Photodermatol. Photoimmunol. Photomed. 15(1):22–7 (1999), reported that lymphocytes treated with psoralen 8-MOP or TMP plus UVA displayed DNA degradation patterns typical of apoptotic cell death. Ozawa, M., et al., J. Exp. Med. 189(4):711–718 (1999), reported that induction of T cell apoptosis could be the main mechanism by which 312-nm UVB resolves psoriasis skin lesions. Low doses of methotrexate may be used to treat psoriasis to restore a clinically normal skin. Heenen, M., et al., Arch. Dermatol. Res. 290(5):240–245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of a compound described herein, which functions as a caspase cascade activator and inducer of apoptosis, should be an effective treatment for psoriasis.

Synovial cell hyperplasia is a characteristic of patients with rheumatoid arthritis (RA). Excessive proliferation of RA synovial cells that, in addition, are defective in synovial cell death might be responsible for the synovial cell hyperplasia. Wakisaka, S., et al., Clin. Exp. Immunol. 114(1): 119–28 (1998), found that, although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells and lead to pannus formation and the destruction of joints in patients with RA. Therefore, an effective amount of a compound, or a pharmaceutically acceptable salt or prodrug of a compound described herein, which functions as a caspase cascade activator and inducer of apoptosis, should be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61(4): 375–80 (1997)). Boirivant, M., et al., Gastroenterology 116(3):557–65 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore, an effective amount of a compound, or a pharmaceutically acceptable salt or prodrug of a compound described herein, which functions as a caspase cascade activator and inducer of apoptosis, should be an effective treatment for inflammation.

Caspase cascade activators and inducers of apoptosis may also be a desirable therapy in the elimination of pathogens, such as HIV, Hepatitis C and other viral pathogens. The long-lasting quiecence, followed by disease progression, may be explained by an anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1 infected asymptomatic individuals (Chinnaiyan, A., et al., *Nat. Med.* 3:333 (1997)). Therefore, apoptosis serves as a beneficial host mechanism to limit the spread of HIV and new therapeutics using caspase/apoptosis activators are useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al., *Hepatology* 3:656–64 (2000)). Therefore, apoptosis inducers are useful as therapeutics for HIV and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with anti-proliferative properties are currently under clinical investigation, including actinomycin D, rapamycin or paclitaxel coated stents (Regar, E., et al., *Br. Med. Bull.* 59:227–248 (2001)). Therefore, apoptosis inducers, which are antiproliferative, are useful as therapeutics for in-stent restenosis.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be orally administered to mammals, e.g. humans, at a dose of 0.0025 to 50 mg/kg, or an equivalent amount of the pharmaceutically acceptable salt thereof, per day of the body weight of the mammal being treated for apoptosis-mediated disorders. Preferably, approximately 0.01 to approximately 10 mg/kg is orally administered to treat or prevent such disorders. For intramuscular injection, the dose is generally approximately one-half of the oral dose. For example, a suitable intramuscular dose would be approximately 0.0025 to approximately 25 mg/kg, and most preferably, from approximately 0.01 to approximately 5 mg/kg. If a known cancer chemotherapeutic agent is also administered, it is administered in an amount which is effective to achieve its intended purpose. The amounts of such known cancer chemotherapeutic agents effective for cancer are well known to those of skill in the art.

The unit oral dose may comprise from approximately 0.01 to approximately 50 mg, preferably approximately 0.1 to approximately 10 mg of the compound of the invention. The unit dose may be administered one or more times daily as one or more tablets, each containing from approximately 0.1 to approximately 10, preferably approximately 0.25 to 50 mg of the compound or its solvates.

In a topical formulation, the compound may be present at a concentration of approximately 0.01 to 100 mg per gram of carrier.

In addition to administering the compound alone, the compounds of the invention may be administered as part of a pharmaceutical preparation containing suitable pharmaceutically acceptable carriers comprising excipients and auxiliaries, which facilitate processing of the compounds into preparations that can be used pharmaceutically. Preferably, the preparations, particularly those preparations, which can be administered orally and which can be used for the preferred type of administration, such as tablets, dragees, and capsules, and also preparations, which can be administered rectally, such as suppositories, as well as suitable solutions for administration by injection or orally, containing from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducer of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducer of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternative, or concurrent, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resultant mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g. maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g. silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally include, e.g. suppositories, which consist of a combination of one or more of the active compounds with a suppository base. Suitable suppository bases are, e.g. natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil; or synthetic fatty acid esters, e.g., ethyl oleate or triglycerides or polyethylene glycol-400 (the compounds are soluble in PEG-400). Aqueous injection suspensions may contain substances, which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil such as almond oil, is admixed. A typical example of such a cream is one which includes approximately: 40 parts water, 20 parts beeswax, 40 parts mineral oil, and 1 part almond oil.

Ointments may be formulated by mixing a solution of the active ingredient in a vegetable oil, such as almond oil with warm soft paraffin and allowing the mixture to cool. A typical example of such an ointment is one which includes approximately: 30% almond oil and 70% white soft paraffin by weight.

The following examples are illustrative, but not limiting, of the method and compositions of the present invention. Other suitable modifications and adaptations of the variety of conditions and parameters normally encountered in clinical therapy, and which are obvious to those skilled in the art, are within the spirit and scope of the invention.

EXAMPLE 1

3-Cyano-1-(4-pyrrolidin-1-yl-benzoyl)-pyrrolo[1,2-a]quinoline a) 1-(4-Pyrrolidin-1-yl-phenacyl)-quinolinium bromide: A stirred solution of 2-bromo-1-(4-pyrrolidin-1-yl-phenyl)-ethanone (689 mg, 2.57 mmol), quinoline (250 μL, 2.11 mmol) and acetonitrile (5.0 mL) was refluxed at 96° C. for 7 h under argon. The solution was equilibrated to room temperature and the precipitate was filtered on a Buchner funnel. The solid was dried in vacuo to yield 812 mg (96%) of the title compound. $^1$H NMR (DMSO-$d_6$): 9.49 (d, J=4.67 Hz, 1H), 9.42 (d, J=8.25 Hz, 1H), 8.54 (d, J=8.24 Hz, 1H), 8.30 (m, 2H), 8.22 (td, J=7.92, 1.31 Hz, 1H), 8.06 (t, J=7.41 Hz, 1H), 7.96 (d, J=8.79 Hz, 2H), 6.84 (s, 2H), 6.72 (d, J=9.07 Hz, 2H), 3.40 (t, J=6.31 Hz, 4H), 2.02 (t, J=6.46 Hz, 4H).

b) 3-Cyano-1-(4-pyrrolidin-1-yl-benzoyl)-pyrrolo[1,2-a]quinoline: A stirred solution of 1-(4-(1-pyrrolidino)-phenacyl)-quinolinium bromide (429 mg, 1.08 mmol), tetrapyridinecobalt(II) dichromate (710 mg, 1.166 mmol), sodium bicarbonate (223 mg, 2.66 mmol), acrylonitrile (360 μL, 5.47 mmol), and N,N-dimethylformamide (3.0 mL) was refluxed at 93° C. for 6 h under argon. The solution was allowed to cool to room temperature, diluted with ethyl acetate (50 mL), then it was filtered to remove some solid. The filtrate was rotary evaporated with heating and the product was purified by flash column chromatography (2:1 hexanes/ethyl acetate) and recrystallized from dichloromethane/ethylacetate to yield 177 mg (45%) of the title compound as a light yellow solid. $^1$H NMR (CDCl$_3$): 8.01 (m, 3H), 7.79 (dd, J=7.69, 1.65 Hz, 1H), 7.65 (d, J=9.34 Hz, 1H), 7.60 (d, J=9.62 Hz, 1H), 7.54 (ddd, J=8.31, 7.01, 1.78 Hz, 1H), 7.47 (td, J=7.49, 1.19 Hz, 1H), 7.30 (s, 1H), 6.62 (dd, J=9.07, 1.93 Hz, 2H), 3.44 (m, 4H), 2.09 (m, 4H).

EXAMPLE 2

1-Benzoyl-3-cyano-6,7,8,9-tetrahydro-pyrrolo[1,2-a]quinoline a) 1-(Phenacyl)-5,6,7,8-tetrahydro-quinolinium bromide: The title compound was prepared from 2-bromo-1-phenyl-ethanone (507.7 mg, 2.55 mmol), 5,6,7,8-tetrahydro-quinoline (275 μL, 2.13 mmol) and acetonitrile (4.2 mL), similar to Example 1a, and yielded 694 mg (98%) as a light tan solid. $^1$H NMR (DMSO-$d_6$): 8.80 (d, J=6.05 Hz, 1H), 8.45 (d, J=7.70 Hz, 1H), 8.11 (d, J=7.97 Hz, 2H), 8.00 (dd, J=7.69, 6.31 Hz, 1H), 7.82 (t, J=7.42 Hz, 1H), 7.68 (t, J=7.56 Hz, 1H), 6.52 (s, 2H), 3.02 (t, J=6.18 Hz, 2H), 2.92 (t, J=6.18 Hz, 2H), 1.85 (m, 2H), 1.77 (m, 2H).

b) 3-Cyano-1-benzoyl-6,7,8,9-tetrahydro-pyrrolo[1,2-a]quinoline: The title compound was prepared from 1-phenacyl-5,6,7,8-tetrahydro-quinolinium bromide (605 mg, 1.82 mmol), tetrapyridinecobalt(II) dichromate (1.20 g, 1.97 mmol), sodium bicarbonate (384 mg, 4.57 mmol), acrylonitrile (600 μL, 9.11 mmol), and N,N-dimethylformamide (8.5 mL), similar to Example 1b, and yielded 230 mg (42%) as a yellow solid. $^1$H NMR (CDCl$_3$): 8.02 (m, 2H), 7.66 (m, 2H), 7.54 (m, 2H), 7.44 (s, 1H), 7.30 (d, J=9.07 Hz, 1H), 2.93 (d, J=6.18 Hz, 1H), 2.68 (d, J=5.91 Hz, 1H), 1.95 (m, 2H), 1.82 (m, 2H).

EXAMPLE 3

3-Benzoyl-1-cyano-indolizine

The title compound was prepared from 1-(phenacyl)-pyridinium bromide (101 mg, 0.362 mmol), tetrapyridinecobalt(II) dichromate (246 mg, 0.403 mmol), sodium bicarbonate (84.9 mg, 1.01 mmol), acrylonitrile (120 μL, 1.82 mmol), and N,N-dimethylformamide (2.0 mL), similar to Example 1b, and yielded 30.5 mg (34%) as a white solid. $^1$H NMR (CDCl$_3$): 9.96 (dd, J=6.05, 1.10 Hz, 1H), 7.82 (m, 3H), 7.61 (m, 2H), 7.52 (m, 3H), 7.17 (td, J=7.00, 1.29 Hz, 1H).

EXAMPLE 4

3-Cyano-1-(3-methoxy-benzoyl)-pyrrollo[1,2-a]quinoline

The title compound was prepared from 1-(3-methoxy-phenacyl)-quinolinium bromide (106 mg, 0.295 mmol), tetrapyridinecobalt(II) dichromate (254 mg, 0.417 mmol), sodium bicarbonate (94.6 mg, 1.13 mmol), acrylonitrile (125 μL, 1.90 mmol), and N,N-dimethylformamide (4.0 mL), similar to Example 1b, and yielded 17.8 mg (19%) as a yellow solid. $^1$H NMR (CDCl$_3$): 8.07 (dd, J=8.51, 0.55 Hz, 1H), 7.85 (dd, J=7.69, 1.65 Hz, 1H), 7.74 (d, J=9.06 Hz, 1H), 7.69–7.58 (m, 4H), 7.54 (td, J=7.48, 1.19 Hz, 1H), 7.48 (d, J=7.96 Hz, 1H), 7.44 (s, 1H), 7.23 (ddd, J=6.87, 2.75, 1.10 Hz, 1H), 3.91 (s, 3H).

EXAMPLE 5

1-(3-Bromo-benzoyl)-3-cyano-pyrrolo[1,2-a]quinoline

The title compound was prepared from 1-(3-bromophenacyl)-quinolinium bromide (150 mg, 0.368 mmol), tetrapyridinecobalt(II) dichromate (306 mg, 0.502 mmol), sodium bicarbonate (96.3 mg, 1.15 mmol), acrylonitrile (150 μL, 2.28 mmol), and N,N-dimethylformamide (4.0 mL), similar to Example 1b, and yielded 21.2 mg (15%) as a yellow solid. $^1$H NMR (CDCl$_3$): 8.20 (t, J=1.79 Hz, 1H), 8.06 (d, J=8.51 Hz, 1H), 7.98 (dt, J=6.25, 1.38 Hz, 1H), 7.86 (dd, J=7.83, 1.51 Hz, 1H), 7.81 (ddd, J=6.52, 2.06, 0.96 Hz, 1H), 7.76 (d, J=9.06 Hz, 1H), 7.69 (d, J=9.06 Hz, 1H), 7.63 (ddd, J=8.31, 7.14, 1.65 Hz, 1H), 7.56 (td, J=7.41, 1.10 Hz, 1H), 7.45 (t, J=7.83 Hz, 1H), 7.44 (s, 1H).

EXAMPLE 6

3-Cyano-1-(4-methyl-benzoyl)-pyrrolo[1,2-a]quinoline

The title compound was prepared from 1-(4-methylphenacyl)-quinolinium bromide (120 mg, 0.350 mmol), tetrapyridinecobalt(II) dichromate (229 mg, 0.376 mmol), sodium bicarbonate (74.7 mg, 0.889 mmol), acrylonitrile (120 μL, 1.82 mmol), and N,N-dimethylformamide (2.5 mL), similar to Example 1b, and yielded 30.6 mg (28%) as a yellow solid. $^1$H NMR (CDCl$_3$): 8.05 (d, J=8.51 Hz, 1H), 7.98 (dd, J=6.60, 1.65 Hz, 2H), 7.84 (dd, J=7.83, 1.51 Hz, 1H), 7.71 (d, J=9.34 Hz, 1H), 7.67 (d, J=9.07 Hz, 1H), 7.60 (ddd, J=8.24, 7.08, 1.58 Hz, 1H), 7.52 (td, J=7.49, 1.19 Hz, 1H), 7.40 (s, 1H), 7.37 (d, J=7.97 Hz, 2H), 2.50 (s, 3H).

EXAMPLE 7

3-Cyano-1-(4-methoxy-benzoyl)-pyrrolo[1,2-a]quinoline

The title compound was prepared from 1-(4-methoxyphenacyl)-quinolinium bromide (110 mg, 0.307 mmol), tetrapyridinecobalt(II) dichromate (202 mg, 0.332 mmol), sodium bicarbonate (66.2 mg, 0.788 mmol), acrylonitrile (110 μL, 1.67 mmol), and N,N-dimethylformamide (2.0 mL), similar to Example 1b, and yielded 26.6 mg (26%) as a yellow solid. $^1$H NMR (CDCl$_3$): 8.08 (dd, J=9.15, 2.20 Hz, 2H), 8.02 (d, J=8.52 Hz, 1H), 7.83 (dd, J=7.55, 1.78 Hz, 1H), 7.70 (d, J=9.34 Hz, 1H), 7.66 (d, J=9.06 Hz, 1H), 7.59 (td, J=7.83, 1.83 Hz, 1H), 7.52 (td, J=7.48, 1.19 Hz, 1H), 7.38 (s, 1H), 7.05 (dd, J=9.25, 2.33 Hz, 2H), 3.94 (s, 3H).

EXAMPLE 8

1-(4-Chloro-benzoyl)-3-cyano-pyrrolo[1,2-a]quinoline

The title compound was prepared from 1-(4-chlorophenacyl)-quinolinium bromide (82.3 mg, 0.227 mmol), tetrapyridinecobalt(II) dichromate (151 mg, 0.248 mmol), sodium bicarbonate (49.5 mg, 0.589 mmol), acrylonitrile (100 μL, 1.52 mmol), and N,N-dimethylformamide (2.0 mL), similar to Example 1b, and yielded 15.6 mg (20%) as a yellow solid. $^1$H NMR (CDCl$_3$): 8.03 (m, 3H), 7.86 (dd, J=7.97, 1.64 Hz, 1H), 7.75 (d, J=9.34 Hz, 1H), 7.68 (d, J=9.34 Hz, 1H), 7.62 (ddd, J=8.31, 7.07, 1.72 Hz, 1H), 7.55 (m, 3H), 7.41 (s, 1H).

EXAMPLE 9

3-Cyano-1-(4-fluoro-benzoyl)-pyrrolo[1,2-a]quinoline

The title compound was prepared from 1-(4-fluorophenacyl)-quinolinium bromide (117 mg, 0.338 mmol), tetrapyridinecobalt(II) dichromate (217 mg, 0.356 mmol), sodium bicarbonate (75.7 mg, 0.901 mmol), acrylonitrile (110 μL, 1.67 mmol), and N,N-dimethylformamide (2.0 mL), similar to Example 1b, and yielded 32.6 mg (30%) as a yellow solid. $^1$H NMR (CDCl$_3$): 8.11 (m, 2H), 8.04 (dd, J=8.52, 0.55 Hz, 1H), 7.86 (dd, J=7.69, 1.65 Hz, 1H), 7.74 (d, J=9.34 Hz, 1H), 7.68 (d, J=9.07 Hz, 1H), 7.62 (ddd, J=8.31, 7.07, 1.72 Hz, 1H), 7.54 (td, J=7.48, 1.19 Hz, 1H), 7.41 (s, 1H), 7.26 (m, 2H).

EXAMPLE 10

3-Cyano-1-(4-nitro-benzoyl)-pyrrolo[1,2-a]quinoline

The title compound was prepared from 1-(4-nitro-phenacyl)-quinolinium bromide (119 mg, 0.319 mmol), tetrapyridinecobalt(II) dichromate (205 mg, 0.336 mmol), sodium bicarbonate (68.3 mg, 0.813 mmol), acrylonitrile (100 μL, 1.52 mmol), and N,N-dimethylformamide (2.0 mL), similar to Example 1b, and yielded 55.0 mg (50%) as a yellow solid. $^1$H NMR (CDCl$_3$): 8.43 (dd, J=9.07, 2.20 Hz, 2H), 8.21 (dd, J=8.88, 2.13 Hz, 2H), 8.12 (d, J=8.52 Hz, 1H), 7.89 (dd, J=7.70, 1.64 Hz, 1H), 7.82 (d, J=9.07 Hz, 1H), 7.71 (d, J=9.06 Hz, 1H), 7.67 (ddd, J=8.17, 7.08, 1.58 Hz, 1H), 7.59 (td, J=7.49, 1.10 Hz, 1H), 7.44 (s, 1H).

EXAMPLE 11

1-(4-Amino-benzoyl)-3-cyano-pyrrolo[1,2-a]quinoline

A solution of 3-cyano-1-(4-nitro-benzoyl)-pyrrolo[1,2-a]quinoline (44.3 mg, 0.130 mmol), 5 wt % Palladium on Carbon (23.4 mg), ethanol (12.0 mL), and ethyl acetate (90.0 mL) was agitated under hydrogen (30 PSI) for 1.5 h. The solution was filtered through Celite and purified by flash column chromatography (9:1 dichloromethane/ethyl acetate) to yield 5.3 mg (13%) of a light brown solid. $^1$H NMR (DMSO-d$_6$): 8.04 (d, J=6.86 Hz, 1H), 7.88 (d, J=9.34 Hz, 1H), 7.81 (d, J=8.79 Hz, 2H), 7.75 (d, J=9.07 Hz, 2H), 7.55–7.70 (m, 3H), 6.66 (d, J=8.79 Hz, 2H), 6.42 (s, 2H).

EXAMPLE 12

1-Benzoyl-3-cyano-5-methyl-pyrrolo[1,2-a]quinoline

The title compound was prepared from 4-methyl-1-phenacyl-quinolinium bromide (86.5 mg, 0.253 mmol), tetrapyridinecobalt(II) dichromate (163 mg, 0.263 mmol), sodium bicarbonate (53.6 mg, 0.638 mmol), acrylonitrile (100 μL, 1.52 mmol), and N,N-dimethylformamide (2.0 mL), similar to Example 1b, and yielded 30.0 mg (38%) as a yellow solid. $^1$H NMR (CDCl$_3$): 8.12 (m, 1H), 8.06 (m, 2H), 7.98 (m, 1H), 7.69 (tt, J=7.37, 1.56 Hz, 1H), 7.53–7.64 (m, 5H) 7.38 (s, 1H), 2.72 (d, J=1.10 Hz, 3H).

EXAMPLE 13

1-Benzoyl-3-cyano-7-methyl-pyrrolo[1,2-a]quinoline

The title compound was prepared from 6-methyl-1-phenacyl-quinolinium bromide (103 mg, 0.300 mmol), tetrapyridinecobalt(II) dichromate (193 mg, 0.317 mmol), sodium bicarbonate (63.4 mg, 0.755 mmol), acrylonitrile (100 μL, 1.52 mmol), and N,N-dimethylformamide (2.0 mL), similar to Example 1b, and yielded 40.2 mg (43%) as a yellow solid. $^1$H NMR (CDCl$_3$): 8.06 (m, 2H), 7.98 (d, J=8.76 Hz, 1H), 7.62–7.71 (m, 4H), 7.57 (t, J=7.56 Hz, 2H), 7.42 (m, 2H), 2.51 (s, 3H).

EXAMPLE 14

3-Cyano-1-(pyridine-2-carbonyl)-pyrrolo[1,2-a]quinoline

A stirred solution of 2-acetylpyridine (450 μL, 4.02 mmol), quinoline (5.0 mL, 42 mmol) and iodine (1.02 g, 4.01 mmol) was refluxed at 105° C. for 2 h under argon. The solution was cooled to room temperature and was concentrated by rotary evaporation in a water bath at 75° C. The residue was dissolved in ethanol (4 mL) and precipitated out by the addition of ethyl acetate (20 mL). The precipitate was filtered and dried in vacuo to yield 384 mg of a brownish-green solid as mixture of the product quinolinium salt and quinoline starting material. The solid (353 mg) was mixed with tetrapyridinecobalt(II) dichromate (591 mg, 0.970 mmol), sodium bicarbonate (199 mg, 2.37 mmol), acrylonitrile (310 μL, 4.71 mmol), and N,N-dimethylformamide (3.0 mL) and was refluxed at 93° C. for 2.5 h. The solution was cooled to room temperature and was concentrated by rotary evaporation. The product was purified by flash column chromatography (7:2 hexanes/ethyl acetate) and was recrystallized from ethyl acetate and dichloromethane to yield 31.6 mg (3% over 2 steps) of the title compound as a yellow solid. $^1$H NMR (CDCl$_3$): 8.80 (dd, J=4.94, 0.82 Hz, 1H), 8.23 (d, J=7.96 Hz, 1H), 8.12 (d, J=8.24 Hz, 1H), 7.98 (td, J=7.76, 1.56 Hz, 1H), 7.85 (m, 2H), 7.76 (d, J=9.06 Hz, 1H), 7.68 (d, J=9.07 Hz, 1H), 7.52–7.65 (m, 3H).

EXAMPLE 15

3-Cyano-1-(pyridine-3-carbonyl)-pyrrolo[1,2-a]quinoline

The quinolinium salt/quinoline mixture was prepared from 3-acetyl-pyridine (440 μL, 4.00 mmol), quinoline (5.0 mL, 42 mmol) and iodine (1.02 g, 4.00 mmol) similar to Example 14, and yielded 312 mg of a brownish-green solid. The title compound was prepared from the quinolinium salt/quinoline mixture (290 mg), tetrapyridinecobalt(II) dichromate (346 mg, 0.568 mmol), sodium bicarbonate (131 mg, 1.56 mmol), acrylonitrile (180 μL, 2.73 mmol), and N,N-dimethylformamide (2.0 mL) similar to Example 14, yielded 15.5 mg (1.3% over 2 steps) as a yellow solid. $^1$H NMR (CDCl$_3$): 8.80 (ddd, J=4.12, 1.65, 0.96 Hz, 1H), 8.24 (d, J=7.97 Hz, 1H), 8.12 (d, J=8.52 Hz, 1H), 7.99 (td, J=7.76, 1.83 Hz, 1H), 7.85 (m, 2H), 7.76 (d, J=9.07 Hz, 1H), 7.69 (d, J=9.06 Hz, 1H), 7.52–7.65 (m, 3H).

EXAMPLE 16

1-Benzoyl-3-cyano-4-methyl-pyrrolo[1,2-a]quinoline a) 3-Methyl-1-phenacyl-quinolinium bromide: The title compound was prepared from 2-bromo-1-phenyl-ethanone (481 mg, 2.405 mmol), 3-methyl-quinoline (296 mg, 2.08 mmol) and acetonitrile (5 mL), similar to Example 1a, and yielded 640 mg (89%) as an off white solid: $^1$H NMR (CDCl$_3$) 0.38 (d, J=1.8 Hz, 1H), 8.74 (s, 1H), 8.31 (m, 1H), 8.28 (m, 1H), 8.17 (dd, J=1.5, 8.4 Hz, 1H), 8.01 (m, 1H), 7.94–7.87 (m, 2H), 7.71 (m, 1H), 7.57 (t, J=7.8 Hz, 2H), 7.49 (s, 2H), 2.81 (s, 3H).

b) 1-Benzoyl-3-cyano-4-methyl-pyrrolo[1,2-a]quinoline: The title compound was prepared from 3-methyl-1-phenacyl-quinolinium bromide (171 mg, 0.50 mmol), tetrapyridinecobalt(II) dichromate (341 mg, 0.56 mmol), sodium bicarbonate (121 mg, 1.44 mmol), acrylonitrile (242 mg, 4.57 mmol), and N,N-dimethylformamide (3 mL), similar to Example 1b, and yielded 64 mg (41%) as a yellow solid: $^1$H NMR (CDCl$_3$) 8.10–8.06 (m, 2H), 7.95–7.92 (m, 1H), 7.77–7.67 (m, 2H), 7.58 (m, 2H), 7.50 (m, 2H), 7.46–7.44 (m, 1H), 7.44 (s, 1H), 2.85 (d, J=0.9 Hz, 3H).

EXAMPLE 17

1-Benzoyl-7-chloro-3-cyano-pyrrolo[1,2-a]quinoline a) 6-Chloro-1-phenacyl-quinolinium bromide: The title compound was prepared from 2-bromo-1-phenyl-ethanone (483 mg, 2.43 mmol), 6-chloro-quinoline (312 mg, 1.91 mmol) and acetonitrile (5 mL), similar to Example 1a, and yielded 433 mg (63%) as an off white solid: $^1$H NMR (CDCl$_3$) 10.40 (d, J=5.7 Hz, 1H), 8.95 (d, J=8.7 Hz, 1H), 8.31 (m, 1H), 8.29 (m 1H), 8.24 (d, J=2.1 Hz, 1H), 8.19–8.14 (m, 2H), 7.99 (dd, J=2.1, 9.3 Hz, 1H), 7.70–7.65 (m, 3H), 7.53 (t, J=7.8 Hz, 2H).

b) 1-Benzoyl-7-chloro-3-cyano-pyrrolo[1,2-a]quinoline: The title compound was prepared from 6-chloro-1-phenacyl-quinolinium bromide (182 mg, 0.50 mmol), tetrapyridinecobalt(II) dichromate (342 mg, 0.56 mmol), sodium bicarbonate (121 mg, 1.44 mmol), acrylonitrile (240 mg, 4.53 mmol), and N,N-dimethylformamide (3 mL), similar to Example 1b, and yielded 25 mg (15%) as a yellow solid: $^1$H NMR (CDCl$_3$) 8.08–8.04 (m, 3H), 7.82 (d, J=2.4 Hz, 1H), 7.73–7.62 (m, 3H), 7.61–7.52 (m, 3H), 7.44 (s, 1H).

EXAMPLE 18

1-Benzoyl-3-cyano-8-methyl-pyrrolo[1,2-a]quinoline a) 7-Methyl-1-phenacyl-quinolinium bromide: The title compound was prepared from 2-bromo-1-phenyl-ethanone (490 mg, 2.46 mmol), 7-methyl-quinoline (302 mg, 2.11 mmol) and acetonitrile (5 mL), similar to Example 1a, and yielded 499 mg (69%) as a light tan solid: $^1$H NMR (CD$_3$OD) 9.28–9.25 (m, 2H), 8.37 (d, J=8.4 Hz, 1H), 8.23–8.19 (m, 2H), 8.13–8.08 (m, 2H), 7.91 (dd, J=0.9, 8.7 Hz, 1H), 7.83–7.78 (m, 1H), 7.70–7.64 (m, 2H), 2.67 (s, 3H).

b) 1-Benzoyl-3-cyano-8-methyl-pyrrolo[1,2-a]quinoline: The title compound was prepared from 7-methyl-1-phenacyl-quinolinium bromide (172 mg, 0.50 mmol), tetrapyridinecobalt(II) dichromate (340 mg, 0.56 mmol), sodium bicarbonate (120 mg, 1.43 mmol), acrylonitrile (240 mg, 4.53 mmol), and N,N-dimethylformamide (3 mL), similar to Example 1b, and yielded 63 mg (40%) as a yellow solid: $^1$H NMR (CDCl$_3$) 8.07 (m, 1H), 8.04 (m, 1H), 7.04 (d, J=0.6 Hz, 1H), 7.74–7.66 (m, 3H), 7.62–7.55 (m, 3H), 7.41 (s, 1H), 7.36 (dd, J=1.2, 8.4 Hz, 1H), 2.52 (s, 3H).

EXAMPLE 19

1-Benzoyl-6-chloro-3-cyano-pyrrolo[1,2-a]quinoline a) 5-Chloro-1-phenacyl-quinolinium bromide: The title compound was prepared from 2-bromo-1-phenyl-ethanone (490 mg, 2.46 mmol), 6-chloro-quinoline (314 mg, 1.92 mmol) and acetonitrile (5 mL), similar to Example 1a, and yielded 394 mg (57%) as a light tan solid: $^1$H NMR (CDCl$_3$) 10.55 (dd, J=1.2, 6.0 Hz, 1H), 9.41 (d, J=8.7 Hz, 1H), 8.32 (m, 1H), 8.30 (m, 1H), 8.23 (dd, J=6.0, 9.0 Hz, 1H), 8.05–7.99 (m, 3H), 7.70 (m, 3H), 7.55 (m, 2H).

b) 1-Benzoyl-6-chloro-3-cyano-pyrrolo[1,2-a]quinoline: The title compound was prepared from 5-chloro-1-phenacyl-quinolinium bromide (180 mg, 0.50 mmol), tetrapyridinecobalt(II) dichromate (340 mg, 0.56 mmol), sodium bicarbonate (120 mg, 1.43 mmol), acrylonitrile (241 mg, 4.54 mmol), and N,N-dimethylformamide (3 mL), similar to Example 1b, and yielded the product as a yellow solid: $^1$H NMR (CDCl$_3$) 8.25 (dd, J=0.6, 9.6 Hz, 1H), 8.08 (m, 1H), 8.06 (m, 1H), 7.97 (m, 1H), 7.78 (d, J=7.8 Hz, 1H), 7.1 (m, 1H), 7.63–7.55 (m, 3H), 7.53–7.48 (m, 1H), 7.45 (s, 1H).

EXAMPLE 20

1-Benzoyl-4-bromo-3-cyano-pyrrolo[1,2-a]quinoline a) 3-Bromo-1-phenacyl-quinolinium bromide: The title compound was prepared from 2-bromo-1-phenyl-ethanone (485 mg, 2.44 mmol), 7-methyl-quinoline (430 mg, 2.07 mmol) and acetonitrile (5 mL), similar to Example 1a, and yielded 303 mg (36%) as a light tan solid: $^1$H NMR (CD$_3$OD) 9.73 (d, J=2.1 Hz, 1H), 9.65 (d, J=1.8 Hz, 1H), 8.44 (dd, J=1.2, 8.1 Hz, 1H), 8.31–8.18 (m, 4H), 8.08 (m, 1H), 7.81 (m, 1H), 6.67 (m, 2H), 6.91 (s, 2H).

b) 1-Benzoyl-4-bromo-3-cyano-pyrrolo[1,2-a]quinoline: The title compound was prepared from 3-bromo-1-phenacyl-quinolinium bromide (90 mg, 0.221 mmol), tetrapyridinecobalt(II) dichromate (150 mg, 0.246 mmol), sodium bicarbonate (61 mg, 0.726 mmol), acrylonitrile (120 mg, 2.26 mmol), and N,N-dimethylformamide (1.5 mL), similar to Example 1b, and yielded the product as a yellow solid: $^1$H NMR (CDCl$_3$) 8.09 (m, 1H), 8.07 (m, 1H), 7.92–7.89 (m, 2H), 7.76 (dd, J=1.8, 7.5 Hz, 1H), 7.71 (m, 1H), 7.62–7.59 (m, 2H), 7.57–7.50 (m, 2H), 7.48 (s, 1H).

EXAMPLE 21

3-Cyano-1-(4-imidazol-1-yl-benzoyl)-pyrrolo[1,2-a]quinoline

A mixture of 3-cyano-(4-fluoro-benzoyl)-pyrrolo[1,2-a]quinoline (8 mg, 0.025 mmol), pottasium carbonate (10 mg, 0.072 mmol) and imidazole (5 mg, 0.073 mmol) were heated in 500 µL of DMF overnight. The reaction mixture was cooled to room temperature, diluted with 10 mL of ethyl acetate, washed with water (3×10 mL), saturated NaCl and the organic layer was dried over anhydrous Na$_2$SO$_4$, filtered and evaporated. The crude was purified by chromatography (3% methanol/chloroform) to yield the title compound (6.9 mg, 75%). $^1$H NMR (CDCl$_3$): 8.21 (dt, J=7.80, 1.20 Hz, 2H), 8.08 (d, J=8.72 Hz, 1H), 8.02 (s, 1H), 7.87 (dd, J=7.81, 1.82 Hz, 1H), 7.73 (m, 2H), 7.60 (m, 4H), 7.46 (s, 1H), 7.42 (t, J=1.24 Hz, 1H), 7.30 (s, 1H).

EXAMPLE 22

3-Cyano-1-[hydroxy-(4-methoxy-phenyl)-methyl]-pyrrolo[1,2-a]quinoline

To a solution of 3-cyano-(4-methoxy-benzoyl)-pyrrolo[1,2-a]quinoline (5.2 mg, 0.0159 mmol) in 5 mL of methanol at room temperature was added sodium borohydride (5.3 mg, 0.14 mmol) and it was stirred overnight at room temperature. Upon the completion of the reaction, 2 drops of aqueous 1N HCl was added and the reaction mixture was evaporated to near dryness. The residue was dissolved in 15 mL of ethyl acetate, washed with water, saturated NaCl and the organic layer was dried over anhydrous Na$_2$SO$_4$, filtered and evaporated. The crude was purified by chromatography (30% ethyl acetate/hexane) to yield the title compound (5.1 mg, 97%). $^1$H NMR (CDCl$_3$): 8.69 (d, J=8.40 Hz, 1H), 7.77 (dd, J=7.80, 1.80 Hz, 1H), 7.57 (m, 2H), 7.47 (m, 1H), 7.38 (m, 3H), 6.95 (dt, J=8.42, 2.12 Hz, 2H), 6.59 (s, 1H), 6.51 (d, J=4.2 Hz, 1H), 3.84 (s, 3H), 2.64 (d, J=4.8, 1H).

EXAMPLE 23

3-Cyano-1-[hydroxy-(4-imidazol-1-yl-phenyl)-methyl]-pyrrolo[1,2-a]quinoline

To a solution of 3-cyano-1-(4-imidazol-1-yl-benzoyl)-pyrrolo[1,2-a]quinoline (40 mg, 0.11 mmol) in 1:1 methanol/chloroform (10 mL) was added sodium borohydride portion-wise over 1 h and the reaction mixture was stirred overnight. It was worked up as described in Example 22 and the crude was purified by chromatography (5% methanol/chloroform) to yield the title compound (38.4 mg, 95%). $^1$H NMR (CDCl$_3$/MeOH-d$_4$): 8.80 (d, J=8.7 Hz, 1H), 7.93 (s, 1H), 7.80 (dd, J=7.8, 1.5 Hz, 1H), 7.53 (m, 8H), 7.38 (t, J=1.2 Hz, 1H), 7.12 (s, 1H), 6.57 (s, broad, 2H).

EXAMPLE 24

3-Cyano-1-cyclopropanecarbonyl-pyrrolo[1,2-a]quinoline a) 1-(2-Cyclopropyl-2-oxo-ethyl)-quinolinium bromide: The title compound was prepared from 2-bromo-1-cyclopropyl ethanone (2.23 g, 13.6 mmol), by a method similar to that described for the preparation of Example 1a, and yielded 2.80 g (70%). $^1$H NMR (DMSO-d6): 9.45 (d, J=5.7 Hz, 1H), 9.40 (d, J=8.1 Hz, 1H), 8.52 (d, J=8.4 Hz, 1H), 8.28 (m, 3H), 8.05 (dd, J=8.1, 1.5 Hz, 1H), 6.53 (s, 2H), 2.48 (m, 1H), 1.18 (m, 2H), 1.05 (m, 2H).

b) 3-Cyano-1-cyclopropanecarbonyl-pyrrolo[1,2-a]quinoline: The title compound was prepared from 1-(2-cyclopropyl-2-oxo-ethyl)-quinolinium bromide (201 mg, 0.688 mmol), by a method similar to that described for the preparation of Example 1b, and yielded 49.4 mg (28%). $^1$H NMR (CDCl$_3$): 8.13 (d, J=8.70 Hz, 1H), 7.86 (s, 1H), 7.77 (dd, J=7.8, 1.5 Hz, 1H), 7.61 (m, 3H), 7.50 (dt, J=7.88, 1.20 Hz, 1H), 2.60 (m, 1H), 1.35 (m, 2H), 1.12 (m, 2H).

EXAMPLE 25

3-Cyano-1-[4-(methyl carboxylate)benzoyl]-pyrrolo[1,2-a]quinoline a) 1-[2-(4-Methoxycarbonyl-phenyl)-2-oxo-ethyl]-quinolinium bromide: The title compound was prepared from 2-bromo-1-(4-methoxy-carbonyl-phenyl) ethanone (1.02 g, 3.98 mmol), by a method similar to that described for the preparation of Example 1a, and yielded 1.47 g (95%). $^1$H NMR (DMSO-$d_6$): 9.54 (dd, J=6.0, 1.2 Hz, 1H), 9.47 (d, J=8.1 Hz, 1H), 8.57 (dd, J=8.1, 0.9 Hz, 1H), 8.53 (d, J=9.0 Hz, 1H), 8.35 (dd, J=8.1, 5.7 Hz, 1H), 8.25 (m, 5H), 8.08 (t, J=7.5 Hz, 1H), 7.07 (s, 2H), 3.95 (s, 3H).

b) 3-Cyano-1-[4-(methyl carboxylate)benzoyl]-pyrrolo[1,2-a]quinoline: The title compound was prepared as described for Example 1b, using 1-[2-(4-methoxycarbonyl-phenyl)-2-oxo-ethyl]-quinolinium bromide (260 mg, 0.670 mmol) and yielded 16.2 mg (7%). $^1$H NMR (CDCl$_3$): 8.23 (m, 2H), 8.11 (m, 3H), 7.87 (dd, J=7.8, 1.50 Hz, 1H), 7.72 (m, 2H), 7.59 (m, 2H), 7.42 (s, 1H), 4.00 (s, 3H).

EXAMPLE 26

3-Cyano-1-(4-diethylamino-benzoyl)-pyrrolo[1,2-a] quinoline a) 1-(4-Diethylamino-phenacyl)-quinolinium bromide: The title compound was prepared from 2-bromo-1-(4-diethylamino phenyl) ethanone (2.23 g, 13.6 mmol), by a method similar to that described for the preparation of Example 1a, and yielded 1.67 g (92%). 1H NMR (DMSO-$d_6$): 9.60 (d, J=6.0 Hz, 1H), 9.52 (d, J=8.4 Hz, 1H), 8.64 (d, J=8.1 Hz, 1H), 8.41 (d, J=9.9 Hz, 1H), 8.39 (d, J=7.5 Hz, 1H), 8.31 (t, J=6.9 Hz, 1H), 8.14 (dd, J=7.8, 6.9 Hz, 1H), 8.04, (d, J=8.7 Hz, 2H), 6.94 (d, J=8.4 Hz, 2H), 6.93 (s, 2H), 3.60 (q, J=8.4 Hz, 4H), 1.26 (t, J=6.6 Hz, 6H).

b) 3-Cyano-1-(4-diethylamino-benzoyl)-pyrrolo[1,2-a]quinoline: The title compound was prepared as described for Example 1b, using 1-(4-diethylamino-phenacyl)-quinolinium bromide (270 mg, 0.679 mmol), and yielded 72.7 mg (29%). $^1$H NMR (CDCl$_3$): 8.00 (m, 3H), 7.79 (dd, J=7.8, 1.8 Hz, 1H), 7.53 (m, 4H), 7.31 (m, 1H), 6.72 (m, 2H), 3.49 (q, J=7.2 Hz, 4H), 1.25 (t, J=7.20 Hz, 6H).

EXAMPLE 27

3-Cyano-1-(4-methanesulfonyl-benzoyl)-pyrrolo[1,2-a]quinoline a) 1-(4-Methanesulfonyl-phenacyl)-quinolinium bromide: The title compound was prepared from 2-bromo-1-(4-methanesulfonyl-phenyl) ethanone (1.03 g, 3.98 mmol), by a method similar to that described for the preparation of Example 1a, and yielded 1.38 g (91%). $^1$H NMR (DMSO-$d_6$): 9.54 (d, J=4.8 Hz, 1H), 9.45 (d, J=8.4 Hz, 1H), 8.57 (m, 2H), 8.36 (m, 3H), 8.24 (m, 3H), 8.08 (t, J=7.8 Hz, 1H), 7.08 (s, 2H), 3.19 (s, 3H).

b) 3-Cyano-1-(4-methanesulfonyl-benzoyl)-pyrrolo[1,2-a]quinoline: The title compound was prepared as described for Example 1b, using 1-(4-methanesulfonyl-phenacyl)-quinolinium bromide (275 mg, 0.679 mmol), and yielded 126 mg (50%). $^1$H NMR (CDCl$_3$): 8.24 (m, 2H), 8.14 (m, 3H), 7.89 (dd, J=7.8, 1.5 Hz, 1H), 7.81 (d, J=9.0 Hz, 1H), 7.70 (d, J=9.30 Hz, 1H), 7.63 (m, 2H), 7.44 (s, 1H), 3.16 (s, 3H).

EXAMPLE 28

3-Cyano-1-[4-(4-methyl-piperazin-1-yl)-benzoyl]-pyrrolo[1,2-a]quinoline

The title compound was prepared as described for the Example 21, using 3-cyano (4-fluoro-benzoyl)-pyrrolo[1,2-a]quinoline (31 mg, 0.0986 mmol) and 4-methyl piperazine (212 mg, 0.212 mmol), and yielded 12.1 mg (68%). $^1$H NMR (CDCl$_3$): 8.01 (m, 3H), 7.82 (dd, J=7.8, 1.8 Hz, 1H), 7.66 (s, 2H), 7.53 (m, 2H), 7.35 (s, 1H), 6.98 (m 2H), 3.70 (t, J=5.1 Hz, 4H), 3.00 (m, 4H), 2.66 (s, 3H).

EXAMPLE 29

3-Cyano-1-(4-morpholin-4-yl-benzoyl)-pyrrolo[1,2-a]quinoline

The title compound was prepared as described for the Example 21, using 3-cyano-(4-fluoro-benzoyl)-pyrrolo[1,2-a]quinoline (30 mg, 0.0954 mmol) and 4-methyl piperazine (243 mg, 0.279 mmol), and yielded 14 mg (38%). $^1$H NMR (CDCl$_3$): 8.02 (m, 3H), 7.81 (dd, J=7.5, 1.5 Hz, 1H), 7.65 (s, 2H), 7.53 (m, 2H), 7.35 (s, 1H), 6.97 (d, J=9.0 Hz, 1H), 3.89 (t, J=4.80 Hz, 4H), 3.39 (t, J=5.10 Hz, 4H).

EXAMPLE 30

3-Cyano-1-[4-(4-pyridin-2-yl-piperazin-1-yl)-benzoyl]-pyrrolo[1,2-a]quinoline The title compound was prepared as described for the Example 21, using 3-cyano-(4-fluoro-benzoyl)-pyrrolo[1,2-a]quinoline (29 mg, 0.0922 mmol) and 4-(4-pyridin-2-yl-piperazine (380 mg, 0.232 mmol), and yielded 18.1 mg (43%). $^1$H NMR (CDCl$_3$): 8.50 (m, 1H), 8.03 (m, 3H), 7.81 (dd, J=7.5, 1.2 Hz, 1H), 7.65 (s, 2H), 7.52 (m, 3H), 7.35 (s, 1H), 7.03 (d, J=9.0 Hz, 2H), 6.69 (m, 2H), 3.78 (m, 4H), 3.60 (m, 4H).

EXAMPLE 31

3-Cyano-1-[4-(2-morpholin-4-yl-ethylamino)-benzoyl]-pyrrolo[1,2-a]quinoline

The title compound was prepared as described for the Example 21, using 3-cyano-(4-fluoro-benzoyl)-pyrrolo[1,2-a]quinoline (31 mg, 0.0986 mmol) and 4-(4-pyridin-2-yl-piperazine (405 mg, 0.311 mmol), and yielded 10.8 mg (26%). $^1$H NMR (CDCl$_3$): 8.00 (m, 3H), 7.80 (dd, J=7.8, 1.8 Hz, 1H), 7.63 (s, 2H), 7.51 (m, 2H), 7.31 (s, 1H), 6.68 (dt, J=8.7, 1.5 Hz, 2H), 3.31 (q, J=6.0 Hz, 2H), 2.71 (t, J=6.0 Hz, 2H), 2.54 (m, 4H).

EXAMPLE 32

3-Cyano-1-[4-(2-phenylamino-ethylamino)-benzoyl]-pyrrolo[1,2-a]quinoline

The title compound was prepared as described for the Example 21, using 3-cyano-(4-fluoro-benzoyl)-pyrrolo[1,2-a]quinoline (30 mg, 0.0954 mmol) and 4-(2-phenylamino)-ethylamine (224 mg, 0.164 mmol), and yielded 17.2 mg (42%). $^1$H NMR (CDCl$_3$): 7.97 (m, 3H), 7.79 (dd, J=7.8, 2.1 Hz, 1H), 7.61 (s, 2H), 7.50 (m, 2H), 7.30 (s, 1H), 7.20 (m, 2H), 6.76 (m, 1H), 6.67 (m, 4H), 4.7 (s, broad, 1H), 3.46 (m, 4H).

EXAMPLE 33

3-Cyano-1-(morpholine-4-carbonyl)-pyrrolo[1,2-a]quinoline a) 1-(2-Morpholin-4-yl-2-oxo-ethyl)-quinolinium chloride: A stirred solution of 2-chloro-1-morpholin-4-yl-ethanone (1.02 g, 6.23 mmol), quinoline (700 µL, 5.91 mmol) and acetonitrile (15.0 mL) was refluxed at 96° C. for 6 h under argon. The solution was equilibrated to room temperature and the precipitate was filtered on a Buchner funnel. The solid was dried in vacuo to yield 349 mg (29%) of the title compound. $^1$H NMR (DMSO-$d_6$): 9.58 (d, J=6.0 Hz, 1H), 9.42 (d, J=8.1 Hz, 1H), 8.53 (d, J=7.8 Hz, 1H), 8.44 (d, J=9.0 Hz, 1H), 8.28 (m, 2H), 8.06 (t, J=7.8 Hz, 1H), 3.82 (t, J=4.2 Hz, 2H), 3.65 (m, 4H), 3.47 (t, J=4.8 Hz, 2H).

b) 3-Cyano-1-(morpholine-4-carbonyl)-pyrrolo[1,2-a]quinoline: The title compound was prepared as described for Example 1b, using 1-(2-morpholin-4-yl-2-oxo-ethyl)-quinolinium chloride (160 mg, 0.539 mmol), and yielded 7.1 mg (4.3%). $^1$H NMR (CDCl$_3$): 7.95 (d, J=8.7 Hz, 1H), 7.81 (dd, J=7.8, 1.8 Hz, 1H), 7.62 (m, 2H), 7.51 (m, 2H), 7.07 (s, 1H), 3.91 (m, 4H), 3.57 (m, 4H).

EXAMPLE 34

3-Cyano-1-(4-pyrazol-1-yl-benzoyl)-pyrrolo[1,2-a]quinoline

The title compound was prepared as described for Example 21, using (4-fluoro-benzoyl)-pyrrolo[1,2-a]quinoline-3-carbonitrile (50 mg, 0.16 mmol) and pyrazole, and yielded 44.9 mg (78%). $^1$H NMR (CDCl$_3$): 8.19 (m, 2H), 8.07 (m, 2H), 7.93 (m, 2H), 7.85 (dd, J=9.6, 1.8 Hz, 1H), 7.82 (d, J=2.1 Hz, 1H), 7.71 (m, 2H), 7.58 (m, 2H), 7.44 (s, 1H), 6.56 (t, J=2.1 Hz, 1H).

EXAMPLE 35

3-Cyano-1-(4-fluoro-benzoyl)-8-methyl-pyrrolo[1,2-a]quinoline a) 1-[2-(4-Fluoro-phenyl)-2-oxo-ethyl]-7-methyl-quinolinium bromide: The title compound was prepared from 2-bromo-(4-fluoro-phenyl) ethanone (0.352 g, 2.46 mmol) and 7-methyl-quinoline (0.71 g, 3.27 mmol), by a method similar to that described for the preparation of Example 1a, and yielded 0.741 g (84%). $^1$H NMR (DMSO-$d_6$): 9.42 (dd, J=16.2, 5.7 Hz, 2H), 8.44 (d, J=8.4 Hz, 1H), 8.35 (s, 1H), 8.24 (m, 3H), 7.92 (d, J=8.4 Hz, 1H), 7.56 (m, 2H), 6.95 (s, 2H), 2.60 (s, 3H).

b) 3-Cyano-1-(4-fluoro-benzoyl)-8-methyl-pyrrolo[1,2-a]quinoline: The title compound was prepared as described for Example 1b, using 1-[2-(4-fluoro-phenyl)-2-oxo-ethyl]-7-methyl-quinolinium bromide (500 mg, 1.39 mmol), and yielded 85.5 mg (19%). $^1$H NMR (CDCl$_3$): 8.09 (m, 2H), 7.85 (s, 1H), 7.72 (m, 2H), 7.60 (d, J=4.7 Hz, 1H), 7.34 (m, 2H), 7.25 (m, 2H), 2.52 (s, 3H).

EXAMPLE 36

3-Cyano-1-(4-imidazol-1-yl-benzoyl)-8-methyl-pyrrolo[1,2-a]quinoline

The title compound was prepared as described for Example 21, using 3-cyano-1-(4-fluoro-benzoyl)-8-methyl-pyrrolo[1,2-a]quinoline (54 mg, 0.164 mmol) and imidazole, and yielded 50.1 mg (81%). $^1$H NMR (CDCl$_3$): 8.20 (dt, J=8.7, 2.1 Hz, 2H), 8.04 (s, broad, 1H), 7.89 (m, 1H), 7.74 (m, 2H), 7.62 (m, 3H), 7.44 (m, 2H), 7.43 (s, broad, 1H), 7.39 (dd, J=7.8, 0.6 Hz, 1H), 7.30 (s, broad, 1H), 2.54 (s, 3H).

EXAMPLE 37

6-Chloro-3-cyano-1-(4-fluoro-benzoyl)-pyrrolo[1,2-a]quinoline

The title compound was prepared as described for Example 1, using 5-Chloro-1-[2-(4-fluoro-phenyl)-2-oxo-ethyl]-quinolinium bromide (673 mg, 1.765 mmol). The crude compound was purified by chromatography (10% ethyl acetate/hexane) to obtain the title compound (44.2 mg, 7.2%). $^1$H NMR (CDCl$_3$): 8.21 (dd, J=9.6, 0.9 Hz, 1H), 8.11 (m, 2H), 7.93 (dd, J=8.7, 0.6 Hz, 1H), 7.76 (d, J=9.3 Hz, 1H), 7.62 (dd, J=7.8, 0.9 Hz, 1H), 7.51 (t, J=8.4 Hz, 1H), 7.43 (s, 1H), 7.26 (t, J=9.0 Hz, 2H).

EXAMPLE 38

6-Chloro-3-cyano-1-(4-imidazol-1-yl-benzoyl)-pyrrolo[1,2-a]quinoline

The title compound was prepared as described for Example 1, using 6-chloro-3-cyano-1-(4-fluoro-benzoyl)-pyrrolo[1,2-a]quinoline (17.4 mg, 0.050 mmol). The crude product was purified by chromatography (3% methanol/dichloromethane) to obtain the title compound (3.2 mg, 16%). $^1$H NMR (CDCl$_3$/MeOH-$d_4$): 8.26 (dd, J=9.6 Hz, 1.2, 1H), 8.21 (m, 2H), 8.04 (m, 1H), 7.97 (dt, J=9.0, 0.9 Hz, 1H), 7.79 (d, J=9.3 Hz, 1H), 7.64 (m, 4H), 7.57 (d, J=6.3 Hz, 1H), 7.44 (m, 1H), 7.32 (m, 1H).

EXAMPLE 39

3-Cyano-1-(hydroxy-phenyl-methyl)-pyrrolo[1,2-a]quinoline

The title compound was prepared as described for Example 22, using 1-benzoyl-3-cyano-pyrrolo[1,2-a]quinoline (9.9 mg, 0.033 mmol), and yielded 7.1 mg (71%). $^1$H NMR (CDCl$_3$): 8.73 (d, J=8.7 Hz, 1H), 7.78 (dd, J=7.8, 1.8 Hz, 1H), 7.60 (m, 1H), 7.53 (d, J=9.3 Hz, 1H), 7.45 (m, 6H), 7.39 (d, J=9.3 Hz, 1H), 6.55 (d, J=5.7 Hz, 1H), 6.52 (s, 1H), 2.74 (d, J=5.4 Hz, 1H).

EXAMPLE 40

3-Cyano-1-[(4-fluoro-phenyl)-hydroxy-methyl]-pyrrolo[1,2-a]quinoline

The title compound was prepared as described for Example 22, using 3-cyano-1-(4-fluoro-benzoyl)-pyrrolo[1,2-a]quinoline (12.6 mg, 0.04 mmol), and yielded 10.3 mg (81%). $^1$H NMR (CDCl$_3$): 8.68 (d, J=8.7 Hz, 1H), 7.77 (dd, J=7.8, 1.5 Hz, 1H), 7.59 (m, 1H), 7.50 (d, J=9.3 Hz, 1H), 7.45 (m, 3H), 7.38 (d, J=9.3 Hz, 1H), 7.10 (m, 2H), 6.53 (d, J=4.8 Hz, 1H), 6.53 (s, 1H), 2.90 (d, J=5.4 Hz, 1H).

EXAMPLE 41

3-Cyano-1-(hydroxy-phenyl-methyl)-8-methyl-pyrrolo[1,2-a]quinoline

The title compound was prepared as described for Example 22, using 1-benzoyl-3-cyano-8-methyl-pyrrolo[1,2-a]quinoline (7.4 mg, 0.238 mmol), and yielded 5.8 mg (78%). $^1$H NMR (CDCl$_3$): 8.50 (s, 1H), 7.64 (d, J=7.8 Hz, 1H), 7.38 (m, 8H), 6.58 (s, 1H), 6.57 (d, J=5.1 Hz, 1H), 2.73 (d, J=5.4 Hz, 1H), 2.50 (s, 3H).

EXAMPLE 42

6-Chloro-3-cyano-1-(hydroxy-phenyl-methyl)-pyrrolo[1,2-a]quinoline

The title compound was prepared as described for Example 22, using 1-benzoyl-6-chloro-3-cyano-pyrrolo[1,2-a]quinoline (8.7 mg, 0.0263 mmol), and yielded 5.3 mg (61%). $^1$H NMR (CDCl$_3$/MeOH-d$_4$): 8.75 (d, J=8.4 Hz, 1H), 7.90 (d, J=9.6 Hz, 1H), 7.48 (m, 8H), 6.59 (s, 1H), 6.43 (s, 1H).

EXAMPLE 43

3-Cyano-1-[hydroxy-(4-pyrazol-1-yl-phenyl)-methyl]-pyrrolo[1,2-a]quinoline

The title compound was prepared as described for Example 22, using 3-cyano-1-(4-pyrazol-1-yl-benzoyl)-pyrrolo[1,2-a]quinoline (7.4 mg, 0.020 mmol), and yielded 5.3 mg (71%). $^1$H NMR (CDCl$_3$/MeOH-d$_4$): 8.79 (d, J=8.7 Hz, 1H), 7.99 (dd, J=2.4, 0.6 Hz, 1H), 7.79 (dd, J=7,8, 1.5 Hz, 1H), 7.71 (m, 3H), 7.57 (m, 4H), 7.47 (m, 2H), 6.60 (s, broad, 1H), 6.55 (s, 1H), 6.51 (dd, J=2.1, 0.5 Hz, 1H).

EXAMPLE 44

3-Cyano-1-(4-piperazin-1-yl-benzoyl)-pyrrolo[1,2-a]quinoline

The title compound was prepared as described for Example 21, using 3-cyano-(4-fluoro-benzoyl)-pyrrolo[1,2-a]quinoline ( 58 mg, 0.185 mmol) and piperazine (102 mg, 1.18 mmol), and yielded 57.2 mg (81%). $^1$H NMR (CDCl$_3$): 8.01 (m, 3H), 7.80 (dd, J=7.8, 1.8 Hz, 1H), 7.64 (s, 2H), 7.52 (m, 2H), 7.34 (d, J=0.6 Hz, 1H), 6.60 (d, J=9.0 Hz, 2H), 3.41 (t, J=5.1 Hz, 4H 3.06 (t, J=4.5 Hz, 4H).

EXAMPLE 45

3-Cyano-1-[4-(3-dimethylamino-propylamino)-benzoyl]-pyrrolo[1,2-a]quinoline

The title compound was prepared as described for Example 21, using 3-cyano-(4-fluoro-benzoyl)-pyrrolo[1,2-a]quinoline (65 mg, 0.206 mmol) and $N^1,N^1$-dimethylpropane-1,3-diamine (200 mg, 1.96 mmol) and yielded 68 mg (83%). $^1$H NMR (CDCl$_3$): 7.98 (m, 2H), 7.81 (dd, J=7.5, 1.8 Hz, 1H), 7.55 (m, 4H), 7.31 (s, 1H), 6.63 (d, J=9.0 Hz, 2H), 5.78 (s, broad, 1H), 3.34 (m, 2H), 2.51 (t, J=6.3 Hz, 2H), 2.31 (s, 6H), 1.85 (m, 2H).

EXAMPLE 46

3-Cyano-1-(4-methoxy-benzoyl)-pyrrolo[1,2-a]quinoxaline a) 1-[2-(4-Methoxy-phenyl)-2-oxo-ethyl]-quinoxalin-1-ium bromide: A mixture of quinoxaline (1.0 g, 7.68 mmol) and 2-bromo-1-(4-methoxy-carbonyl-phenyl) ethanone (2.0 g, 8.73 mmol) was heated at 60° C. for 10 minutes and 5 mL of ethyl acetate was added, continued to stirr for another 10 minutes. The off white precipitate was filtered on a Buchner funnel. The solid was dried in vacuo to yield 228 mg (8%) of the title compound. $^1$H NMR (DMSO-d$_6$): 9.86 (d, J=2.4 Hz, 1H), 9.62 (d, J=2.4 Hz, 1H), 8.60 (m, 2H), 8.32 (m 2H), 8.14 (d, J=8.7 Hz, 2H), 7.23 (d, J=9.0 Hz, 2H), 7.10 (s, 2H), 3.92 (s, 3H).

b) 3-Cyano-1-(4-methoxy-benzoyl)-pyrrolo[1,2-a]quinoxaline: A stirred solution of 1-[2-(4-methoxy-phenyl)-2-oxo-ethyl]-quinoxalin-1-ium bromide (214 mg, 0.596 mmol), manganese dioxide (418 mg, 4.81 mmol), tri-ethyl amine (165 µL, 1.19 mmol), acrylonitrile (200 µL, 3.04 mmol), and N,N-dimethylformamide (3.0 mL) was refluxed at 93° C. for 5 h under argon. The solution was cooled to room temperature and diluted with 100 mL of ethyl acetate, filtered, and the filtrate was washed with water (3×50 mL), saturated NaCl, dried over Na$_2$SO$_4$, filtered and evaporated under vacuum. The residue was purified by flash chromatography (25% ethyl acetate/hexane) to yield 66.8 mg (34%) of the title compound. $^1$H NMR (CDCl$_3$): 8.14 (dd, J=7.8, 1.8 Hz, 1H), 8.04 (m, 3H), 7.60 (m, 2H), 7.40 (s, 1H), 7.05 (m, 2H), 3.95 (s, 3H).

EXAMPLE 47

3-Cyano-1-(4-methoxy-benzoyl)-4,5-dihydro-pyrrolo[1,2-a]quinoxaline

A mixture of 3-cyano-1-(4-methoxy-benzoyl)-pyrrolo[1,2-a]quinoxaline (14.5 mg, 0.0044 mmol) in 10 mL of methanol and 0.5 mL acetone was hydrogenated on PtO$_2$ at 40 psi for 4 h. The reaction mixture was filtered, concentrated under vacuum and the residue was purified by chromatography (25% ethyl acetate/hexane) to yield 7.2 mg (50%) of the title compound. $^1$H NMR (CDCl$_3$): 7.97 (m, 2H), 6.97 (m, 7H), 4.48 (s, 2H), 4.25 (s, broad, 1H), 3.92 (s, 3H).

EXAMPLE 48

3-Cyano-1-(3-hydroxy-benzoyl)-pyrrolo[1,2-a]quinoline

A mixture of 3-cyano-1-(3-methoxybenzoyl)-pyrrolo[1,2-a]quinoline (326 mg, 1 mmol), tetrabutylammonium bromide (967 mg, 3 mmol), potassium iodide (498 mg, 3 mmol), boron tribromide (1N solution in dichloromethane, 3 ml) in dichloromethane (5 ml) was refluxed for 8 h. It was cooled to room temperature and quenched with water (20 mL), the organic layer was washed with aqueous sodium bicarbonate (2×10 mL), water (2×20 mL), dried over Na$_2$SO$_4$, and concentrated. The residue was purified by column chromatography to give 188 mg (60%) of title compound. $^1$H NMR (CDCl$_3$): 8.06 (d, J=9.0 Hz, 1H), 7.85 (d, J=7.80 Hz, 1H), 7.74–7.40 (m, 8H), 7.20–7.14 (m, 1H), 5.15 (s, 1H).

EXAMPLE 49

3-Cyano-1-[3-(2-morpholin-4-yl-ethoxy)benzoyl]-pyrrolo[1,2-a]quinoline

A mixture of 3-cyano-1-(3-hydroxy-benzoyl)-pyrrolo[1,2-a]quinoline (31.2 mg, 0.1 mmol), 4-(2-chloroethyl)morpholine hydrochloride (37.2 mg, 0.2 mmol), potassium carbonate (165 mg, 1 mmol) in acetone (5 mL) was refluxed for 4 h. It was evaporated to dryness and the residue was purified by column chromatography (EtOAc) to give 16 mg (37%) of the title compound. $^1$H NMR (CDCl$_3$): 8.06 (d, J=8.7 Hz, 1H), 7.86–7.83 (m, 1H), 7.75–7.43 (m, 8H), 7.26–7.20 (m, 1H), 4.20 (t, J=5.60 Hz, 2H), 3.74 (t, J=4.80 Hz, 4H), 2.85 (t, J=5.40 Hz, 2H), 2.60 (t, (t, J=4.50 Hz, 4H).

Compounds of Examples 50–52 were prepared by a procedure similar to Example 49 from 3-cyano-1-[3-hydroxy-benzoyl]-pyrrolo[1,2-a]quinoline.

EXAMPLE 50

3-Cyano-1-[3-(2-dimethylamino-ethoxy)benzoyl]-pyrrolo[1,2-a]quinoline $^1$H NMR (CDCl3): 8.06 (d, J=8.7 Hz, 1H), 7.86–7.83 (m, 1H), 7.75–7.43 (m, 8H), 7.28–7.24 (m, 1H), 4.16 (t, J=5.40 Hz, 2H), 2.78 (t, J=5.40 Hz, 4H), 2.36 (s, 1H).

EXAMPLE 51

3-Cyano-1-[3-(carboxymethoxy)benzoyl]-pyrrolo[1,2-a]quinoline $^1$H NMR (CDCl$_3$): 8.06 (d, J=8.4 Hz, 1H), 7.87–7.83 (q, J$_1$=7.80 Hz, J$_2$=1.5 Hz, 1H), 7.75–7.43 (m, 8H), 7.30–7.24 (m, 1H), 4.80 (s, 1H).

EXAMPLE 52

3-Cyano-1-[3-(2-hydroxyethoxy)benzoyl]-pyrrolo[1,2-a]quinoline $^1$H NMR (CDCl$_3$): 8.06 (d, J=7.8 Hz, 1H), 7.86–7.83 (m, 1H), 7.76–7.43 (m, 8H), 7.28–7.24 (m, 1H), 4.19 (t, J=4.20 Hz, 2H), 4.02 m, 2H), 2.02 (t, J=6.3 Hz, 1H).

EXAMPLE 53

3-Cyano-1-[2-(dimethylaminomethyl)benzoyl]-pyrrolo[1,2-a]quinoline a) 3-cyano-1-[2-(bromomethyl)benzoyl]-pyrrolo[1,2-a]quinoline. A solution of cyano-1-(2-methyl-benzoyl)-pyrrolo[1,2-a]quinoline (110 mg, 0.6 mmol), NBS (139 mg, 0.78 mmol) and AIBN (116 mg, 0.72) in carbon tetrachloride (10 mL) was refluxed for 3 h, it was evaporated and the residue was purified by column chromatography to give 35 mg (25%) of 3-cyano-1-[2-(bromomethyl)benzoyl]-pyrrolo[1,2-a]quinoline.

b) 3-cyano-1-[2-(dimethylaminomethyl)benzoyl]-pyrrolo[1,2-a]quinoline. A solution of 3-cyano-1-[2-(bromomethyl)benzoyl]-pyrrolo[1,2-a]quinoline (8 mg, 0.02 mmol) and dimethylamine (2M solution in THF, 1 mL) in THF (2 mL) was stirred at room temperature for 1 h. It was evaporated and the residue was purified by column chromatography (Hexane/EtOAc 2:1) to give 6 mg (85%) of the title compound. $^1$H NMR (CDCl$_3$): $^1$H NMR (CDCl$_3$): 8.06 (d, J=9.0 Hz, 1H), 7.84–7.80 (q, J$_1$=7.80 Hz, J$_2$=1.5 Hz, 1H), 7.72–7.33 (m, 8H), 7.05 (s, 1H), 3.49 (s, 2H), 1.90 (s, 6H).

EXAMPLE 54

3-Cyano-1-[4-(dimethylaminomethyl)benzoyl]-pyrrolo[1,2-a]quinoline a) 3-Cyano-1-[4-(bromomethyl)benzoyl]-pyrrolo[1,2-a]quinoline. The title compound was prepared similar as Example 53a, using 3-cyano-1-(4-methylbenzoyl)-pyrrolo[1,2-a]quinoline to yield 230 mg (68%). $^1$H NMR (CDCl$_3$): 8.09–8.10 (m, 3H), 7.87–7.52 (m, 7H), 7.43 (s, 1H), 4.58 (s, 2H).

b) 3-Cyano-1-[4-(dimethylaminomethyl)benzoyl]-pyrrolo[1,2-a]quinoline. The title compound was prepared similar as Example 53b, using 3-cyano-1-[4-(bromomethyl)benzoyl]-pyrrolo[1,2-a]quinoline and dimethylamine, yield 5 mg (18%). $^1$H NMR (CDCl$_3$): 8.09–8.10 (m, 3H), 7.87–7.52 (m, 7H), 7.42 (s, 1H), 3.57 (s, 2H), 2.32 (s, 6H).

Compounds of Examples 55–57 were prepared by a procedure similar to Example 54b from 3-cyano-1-[4-(bromomethyl)benzoyl]-pyrrolo[1,2-a]quinoline.

EXAMPLE 55

3-Cyano-1-[4-(morpholin-4-ylmethyl)benzoyl]-pyrrolo[1,2-a]quinoline $^1$H NMR (CDCl$_3$): 8.08–8.01 (m, 3H), 7.87–7.52 (m, 7H), 7.42 (s, 1H), 3.76 (t, J=4.8 Hz, 4H), 3.63 (s, 2H), 2.51 (t, J=4.8 Hz, 4H).

EXAMPLE 56

3-Cyano-1-[4-(4-methylpiperazin-1-ylmethyl)benzoyl]-pyrrolo[1,2-a]quinoline $^1$H NMR (CDCl$_3$): 8.08–8.01 (m, 3H), 7.87–7.52 (m, 7H), 7.42 (s, 1H) 3.64 (s, 2H), 2.55 (bs, 4H), 2.33 (s, 3H), 2.05 (bs, 4H).

EXAMPLE 57

3-Cyano-1-[4-(imidazol-1-ylmethyl)benzoyl]-pyrrolo[1,2-a]quinoline $^1$H NMR (CDCl$_3$): 8.08–8.04 (d, J=8.1 Hz 1H), 8.00–6.90 (m, 13H), 5.28 (s, 3H).

EXAMPLE 58

3-Cyano-1-(4-fluoro-benzoyl)-8-dimethylaminomethyl-pyrrolo[1,2-a]quinoline

The title compound was prepared by a procedure similar to Example 53a and 53b, starting from 3-cyano-1-(4-fluorobenzoyl)-8-methyl-pyrrolo[1,2-a]quinoline. $^1$H NMR (CDCl$_3$): 8.11–8.05 (m, 2H), 7.94 (s, 1H), 7.82–7.55 (m, 4H), 7.40 (s, 1H), 7.28–7.20(m, 2H), 3.57 (s, 2H), 2.25 (s, 6H).

EXAMPLE 59

3-Cyano-1-(4-dimethylamino-benzoyl)-pyrrolo[1,2-a]quinoline

A solution of 3-cyano-1-[4-fluoro-benzoyl]-pyrrolo[1,2-a]quinoline (56 mg, 0.18 mmol) and dimethylhydrazine (118 mg, 1.96 mmol) in DMF (5 mL) was refluxed for 24 h. It was diluted with water (50 mL) and extracted with EtOAc (3×20 mL). The combined organic layers were dried, concentrated and the residue was purified by column chromatography (EtOAc/Hexane 6:1) to give 15 mg (25%) of the title compound. $^1$H NMR (CDCl$_3$): 8.11–8.05–7.95 (m, 3H), 7.82–7.78 (m, 2H), 7.63–7.42 (m, 4H), 7.31 (s, 1H), 6.75 (d, J=9.30 Hz, 2H), 3.14 (s, 6H). MS, 340 (M+1).

Compounds of Examples 60–62 were prepared in two steps by a procedure similar to that of Example 1.

EXAMPLE 60

1-Benzoyl-3-cyano-6-nitro-pyrrolo[1,2-a]quinoline $^1$H NMR (CDCl$_3$): 8.36–8.31 (m, 2H), 8.18 (dd, J=1.2, 8.1 Hz, 1H), 8.09 (m, 1H), 8.06 (m, 1H), 7.87 (d, J=9.6 Hz, 1H), 7.76–7.66 (m, 2H), 7.63–7.58 (m, 2H), 7.50 (s, 1H).

EXAMPLE 61

1-Benzoyl-3-cyano-6-hydroxy-pyrrolo[1,2-a]quinoline $^1$H NMR (CDCl$_3$): 8.15 (dd, J=0.9, 9.6 Hz, 1H), 8.09 (m, 1H), 8.07 (m, 1H), 7.70 (m, 1H), 7.64 (d, J=9.3 Hz, 1H), 7.60–7.53 (m, 3H), 7.42 (s, 1H), 7.39 (t, J=8.7 Hz, 1H), 6.85 (dd, J=0.9, 7.8 Hz, 1H), 5.78 (s, 1H).

EXAMPLE 62

1-Benzoyl-3-cyano-8-hydroxy-pyrrolo[1,2-α]quinoline $^1$H NMR (CDCl$_3$): 8.15 (br s, 1H), 7.82–7.79 (m, 2H), 7.73–7.70 (m, 3H), 7.58 (m, 1H), 7.51 (d, J=9.1 Hz, 1H), 7.40–7.35 (m, 3H), 7.01 (dd, J=2.4, 8.7 Hz, 1H).

EXAMPLE 63

1-Benzoyl-3-cyano-6-(2-morpholin-4-yl-ethoxy)-pyrrolo[1,2-a]quinoline

A mixture of 1-benzoyl-3-cyano-6-hydroxy-pyrrolo[1,2-α]quinoline (31 mg, 0.10 mmol), N-(2-chloro-ethyl)-morpholine hydrochloride (25 mg, 0.13 mmol), potassium carbonate (138 mg, 1.0 mmol) and potassium iodide (18 mg, 0.11 mmol) in anhydrous acetone (10 mL) was heated in 60° C. oil bath for 2.5 days. The solvent was evaporated, and the residue was stirred with EtOAc (25 mL) and filtered. The EtOAc filtrate was evaporated and the crude product was purified by chromatography (SiO$_2$, EtOAc/hexanes 50 to 100%) to give a light yellow solid (18 mg, 42%): $^1$H NMR (CDCl$_3$): 8.21 (d, J=9.6, Hz, 1H), 8.08 (m, 1H), 8.05 (m, 1H), 7.71–7.47 (m, 6H), 7.42 (s, 1H), 6.94 (d, J=7.2 Hz, 1H), 4.33 (t, J=6.0 Hz, 2H), 3.76 (t, J=4.8 Hz, 4H), 2.97 (t, J=6.0 Hz, 2H), 2.65 (t, J=4.5 Hz, 4H).

Compounds of Examples 64–66 were prepared by a procedure similar to that of Example 63.

EXAMPLE 64

1-Benzoyl-3-cyano-6-(2-dimethylamino-ethoxy)-pyrrolo[1,2-a]quinoline $^1$H NMR (CDCl$_3$): 8.04–8.01 (m, 2H), 7.76–7.66 (m, 3H), 7.59–7.54 (m, 4H), 7.44 (s, 1H), 7.20 (dd, J=2.1, 8.7 Hz, 1H), 4.11 (t, J=5.4 Hz, 2H), 2.78 (t, J=5.4 Hz, 2H), 2.32 (s, 6H).

EXAMPLE 65

1-Benzoyl-3-cyano-8-(2-morpholin-4-yl-ethoxy)-pyrrolo[1,2-a]quinoline $^1$H NMR (CDCl$_3$): 8.04–8.01 (m, 2H), 7.76 (d, J=8.7 Hz, 1H), 7.72–7.67 (m, 2H), 7.60–7.55 (m, 4H), 7.45 (s, 1H), 7.18 (dd, J=2.1, 9.0 Hz, 1H), 4.16 (t, J=5.7 Hz, 2H), 3.67 (m, 4H), 2.81 (t, J=5.7 Hz, 2H), 2.53 (m, 4H).

EXAMPLE 66

1-Benzoyl-3-cyano-8-(2-dimethylamino-ethoxy)-pyrrolo[1,2-a]quinoline $^1$H NMR (CDCl$_3$): 8.23 (d, J=9.3 Hz, 1H), 8.07–8.04 (m, 2H), 7.71–7.47 (m, 6H), 7.41 (s, 1H), 6.95 (d, J=8.1 Hz, 1H), 4.33 (t, J=5.7 Hz, 2H), 2.97 (t, J=5.7 Hz, 2H), 2.46 (s, 6H).

EXAMPLE 67

1-(3-Methoxy-benzoyl)-pyrrolo[1,2-a]quinoline-3-carboxylic acid

A solution of 1-(3-methoxy-benzoyl)-pyrrolo[1,2-a]quinoline-3-carboxylic acid, methyl ester (130 mg, 0.348 mmol) in MeOH (5 mL) and NaOH (2N, 5 mL) was stirred at 50° C. for 24 h. The reaction mixture was acidified to pH=3 with 10% HCl to produce a light yellow precipitate. The mixture was filtered and the solid was washed with water, and dried in vacuo (114 mg, 95%): $^1$H NMR (DMSO-D$_6$): 8.28 (d, J=9.3 Hz, 1H), 8.04 (dd, J=1.2, 8.7 Hz, 1H), 7.97 (d, J=9.3 Hz, 2H), 7.70–7.52 (m, 5H), 7.46 (s, 1H), 7.33 (m, 1H), 3.86 (s, 3H), 3.35 (s, 1H).

EXAMPLE 68

1-(3-Methoxy-benzoyl)-pyrrolo[1,2-a]quinoline-3-carboxylic acid N-hydroxysuccinimidyl ester A mixture of 1-(3-methoxy-benzoyl)-pyrrolo[1,2-a]quinoline-3-carboxylic acid (126 mg, 0.4 mmol), N-hydroxysuccinimide (96 mg, 0.8 mmol) and 1,3-dicyclohexycarbodiimide (165 mg, 0.8 mmol) in dichloromethane (10 mL) was stirred at room temperature for 7 h. The reaction was filtered to remove the insoluble material. The filtrate was concentrated under reduced pressure and the residue was purified by chromatography (SiO$_2$, EtOAc:hexanes 20–100%) to give a yellow solid: $^1$H NMR (CDCl$_3$): 8.25 (d, J=9.3 Hz, 1H), 8.06 (d, J=8.7 Hz, 1H), 7.87 (dd, J=1.5, 7.8 Hz, 1H), 7.82 (d, J=9.0 Hz, 2H), 7.79 (s, 1H), 7.71–7.60 (m, 3H), 7.55 (dt, J=1.2, 7.5 Hz, 1H), 7.47 (t, J=7.8 Hz, 1H), 7.23 (ddd, J=0.9, 2.7, 8.4 Hz, 1H), 3.91 (s, 3H), 2.91 (s, 4H).

EXAMPLE 69

1-(3-Methoxy-benzoyl)-pyrrolo[1,2-a]quinoline-3-carboxylic acid (2-hydroxy-ethyl)-amide A mixture of 1-(3-methoxy-benzoyl)-pyrrolo[1,2-a]quinoline-3-carboxylic acid, N-hydroxysuccinimidyl ester (15 mg, 0.034 mmol) and ethanolamine (61 mg, 1 mmol) in dichloromethane was stirred at room temperature for 2 h. The reaction mixture was diluted with EtOAc (20 mL), washed with water (2 mL), and dried with MgSO4 and evaporated to give a yellow semi-solid (14 mg): $^1$H NMR (CDCl$_3$): 8.42 (d, J=9.3 Hz, 1H), 8.00 (d, J=8.4 Hz, 1H), 7.79 (dd, J=1.5, 7.5 Hz, 1H), 7.64–7.60 (m, 2H), 7.57–7.41 (m, 4H), 7.32 (s, 1H), 7.19 (ddd, J=1.2, 2.7, 8.4 Hz, 1H), 6.48 (t, J=5.7 Hz, 1H), 3.88 (s, 3H), 3.77 (t, J=4.8 Hz, 2H), 3.53 (dd, J=5.4, 9.9 Hz, 2H), 2.2 (br s, 1H).

Compounds of Examples 70–76 were prepared by a procedure similar to that of Example 69.

EXAMPLE 70

1-(3-Methoxy-benzoyl)-pyrrolo[1,2-a]quinoline-3-carboxylic acid (2-morpholin-4-yl-ethyl)-amide $^1$H NMR (CDCl$_3$): 8.45 (d, J=9.3 Hz, 1H), 8.06 (d, J=7.8 Hz, 1H), 7.80 (dd, J=1.5, 7.8 Hz, 1H), 7.68–7.44 (m, 6H), 7.34 (s, 1H), 7.21 (m, 1H), 6.48 (m, 1H), 3.90 (s, 3H), 3.68 (t, J=7.8 Hz, 4H), 3.54 (dd, J=6.0, 11.0 Hz, 2H), 2.59 (t, J=6, 2H), 2.50 (m, 4H).

EXAMPLE 71

1-(3-Methoxy-benzoyl)-pyrrolo[1,2-a]quinoline-3-carboxylic acid hydroxy-amide $^1$H NMR (CDCl$_3$): 8.29 (d, J=9.3 Hz, 1H), 8.06 (d, J=8.4 Hz, 1H), 7.98 (d, J=8.4 Hz, 1H), 7.85–7.72 (m, 3H), 7.68 (s, 1H), 7.65–7.44 (m, 4H), 7.22 (m, 1H), 6.60 (s, 1H), 3.90 (s, 3H); MS 361 (M+1).

EXAMPLE 72

1-(3-Methoxy-benzoyl)-pyrrolo[1,2-a]quinoline-3-carboxylic acid (2-amino-ethyl)-amide $^1$H NMR (CDCl$_3$): 8.47 (d, J=9.6 Hz, 1H), 8.02 (d, J=8.7 Hz, 1H), 7.84 (dd, J=1.8, 7.8 Hz, 1H), 7.66–7.40 (m, 7H), 7.20 (dd, J=2.4, 9.0 Hz, 1H), 6.60 (br s, 1H), 3.89 (s, 3H), 3.49 (m, 2H), 2.94 (br s, 2H), 1.97 (m, 2H); MS 388 (M+1).

EXAMPLE 73

1-(3-Methoxy-benzoyl)-pyrrolo[1,2-a]quinoline-3-carboxylic acid (3-dimethylamino-propyl)-amide $^1$H NMR (CDCl$_3$): 8.54 (d, J=9.6 Hz, 1H), 8.51 (m, 1H), 8.12 (d, J=8.1 Hz, 1H), 7.79 (dd, J=1.5, 7.8 Hz, 1H), 7.64–7.53 (m, 4H), 7.49–7.42 (m, 2H), 7.30 (s, 1H), 7.19 (ddd, J=0.9, 2.4, 8.4 Hz, 1H), 3.89 (s, 3H), 3.54 (dd, J=6.0, 10.5 Hz, 2H), 2.48 (t, J=6.0 Hz, 2H), 2.11 (s, 6H), 1.73 (p, J=6.0 Hz, 2H); MS 430 (M+1).

EXAMPLE 74

1-(3-Methoxy-benzoyl)-pyrrolo[1,2-a]quinoline-3-carboxylic acid {2-[2-(2-amino-ethoxy)-ethoxy-]-ethyl}-amide $^1$H NMR (CDCl$_3$): 8.50 (d, J=9.6 Hz, 1H), 5.39 (d, J=8.7 Hz, 1H), 7.79 (dd, J=1.5, 4.5 Hz, 1H), 7.68–7.44 (m, 7H), 7.20 (ddd, J=0.6, 2.4, 8.1 Hz, 1H), 6.94 (m, 1H), 3.90 (s, 3H), 3.60 (m, 8H), 3.44 (t, J=5.1 Hz, 2H), 2.73 (s, 2H), 1.90 (m, 2H); MS 476 (M+1).

EXAMPLE 75

1-(3-Methoxy-benzoyl)-3-(4-methyl-piperazine-1-carbonyl)-pyrrolo[1,2-a]quinoline $^1$H NMR (CDCl$_3$): 8.03 (d, J=8.1 Hz, 1H), 7.79 (m, 2H), 7.65 (m, 1H), 7.60–7.41 (m, 5H), 7.26 (s, 1H), 7.20 (ddd, J=1.2, 3.0, 8.4 Hz, 1H), 3.89 (s, 3H), 3.73 (s, 4H), 2.43 (s, 4H), 2.32 (s, 3H); MS 428 (M+1).

EXAMPLE 76

1-(3-Methoxy-benzoyl)-pyrrolo[1,2-a]quinoline-3-carboxylic acid (2-piperazin-1-yl-ethyl)-amide $^1$H NMR (CDCl$_3$): 8.45 (d, J=9.3 Hz, 1H), 8.05 (d, J=8.7 Hz, 1H), 7.80 (dd, J=1.5, 8.1 Hz, 1H), 7.65–7.43 (m, 6H), 7.38 (d, J=0.6 Hz, 1H), 7.21 (ddd, J=1.2, 2.7, 7.2 Hz, 1H), 6.60 (m, 1H), 3.90 (s, 3H), 3.54 (dd, J=6.0, 11.1 Hz, 2H), 2.85 (m, 4H), 2.58 (t, J=6.0 Hz, 2H), 2.47 (m, 4H), 1.80 (s 1H).

Compounds of Examples 77–80 were prepared in two steps by a procedure similar to that of Example 1.

EXAMPLE 77

3-Cyano-1-(2-fluoro-benzoyl)-pyrrolo[1,2-a]quinoline $^1$H NMR (CDCl$_3$): 8.30 (8.7, d, 1H), 7.74–8.86 (m, 3H), 7.53–7.68 (m, 4H), 7.42 (d, J=3 Hz, 1H), 7.30–7.36 (m, 1H), 7.23 (m, 1H).

EXAMPLE 78

3-Cyano-1-(2-methylbenzoyl)-pyrrolo[1,2-a]quinoline $^1$H NMR (CDCl$_3$): 8.328 (d, J=8.4 Hz, 1H), 7.87–7.30 (m, 10H), 2.50 (s, 3H).

EXAMPLE 79

3-Cyano-1-(4-acetamido-3-nitro-benzoyl)-pyrrolo[1,2-a]quinoline $^1$H NMR (CDCl$_3$): 10.6 (s, broad, 1H), 9.06 (d, 9, 1H), 8.96 (d, 2.4, 1H), 8.34 (dd, 9, 2.1, 1H), 8.03 (d, 7.8, 1H), 7.88 (dd, 7.8, 1.5, 1H), 7.69–7.80 (m, 2H), 7.54–7.67 (m, 2H), 7.44 (s, 1H), 2.39 (s, 3H).

EXAMPLE 80

3-Cyano-1-(4-fluoro-benzoyl)-pyrrolo[1,2-a]quinoxaline $^1$H NMR (CDCl$_3$): 9.21 (s, 1H), 8.05–8.18 (m, 4H), 7.58–7.69 (m, 2H), 7.44 (s, 1H), 7.25–7.31 (m, 2H).

Compounds of Examples 81–82 were prepared in two steps by a procedure similar to that of Example 21.

EXAMPLE 81

3-Cyano-1-(2-imidazol-1-yl-benzoyl)-pyrrolo [1,2-a]quinoline $^1$H NMR (CDCl$_3$): 8.31 (8.6, d, 1H), 7.79–7.83 (m, 2H), 7.61–7.77 (m, 5H), 7.48–7.52 (m, 2H), 7.24 (m, 1H), 7.04 (m, 2H), 6.93 (m, 1H).

EXAMPLE 82

3-Cyano-1-(2-morpholine-1-yl-benzoyl)-pyrrolo[1,2-a]quinoline $^1$H NMR (CDCl$_3$): 8.33–8.39 (m, 1H), 7.83–7.86 (m, 1H), 7.51–7.74 (m, 6H), 7.15–7.29 (m, 3H), 3.46–3.49 (m, 4H), 2.98–3.02 (m, 4H).

EXAMPLE 83

3-Cyano-1-(4-carboxy-benzoyl)-pyrrolo[1,2-a]quinoline

3-Cyano-1-(4-methoxycarbonyl-benzoyl)-pyrrolo[1,2-a]quinoline (10 mg, 0.028 mmol) was disolved in a mixture of 5 mL of THF and 0.5 mL of ethyl alcohol and 1 mL of 2M NaOH was added and the mixture was stirred for 4 h at 50° C. The mixture was cooled to 0° C., acidified using 2N HCl and the resulting precipitate was collected, washed with cold ethyl alcohol and dried under vacuum (9.6 mg, 99%). $^1$H NMR (DMSO): 8.11–7.99 (m, 5H), 7.80–7.83 (m, 2H), 7.61–7.72 (m, 4H).

EXAMPLE 84

Identification of 1-Benzoyl-3-cyano-pyrrolo[1,2-a]quinoline and other Analogs as Antineoplastic Compounds that are Caspase Cascade Activators and Apoptosis Inducers Human breast cancer cell lines T-47D and ZR-75-1 were grown according to media component mixtures designated by American Type Culture Collection +10% FCS (Invitrogen Corporation), in a 5% $CO_2$–95% humidity incubator at 37° C. T-47D and ZR-75-1 cells were maintained at a cell density between 30 and 80% confluency and for HL-60 at a cell density of 0.1 to 0.6×10$^6$ cells/mL. Cells were harvested at 600×g and resuspended at 0.65×10$^6$ cells/mL into appropriate media +10% FCS. An aliquot of 45 µL of cells was added to a well of a 96-well microtiter plate containing 5 µL of a 10% DMSO in RPMI-1640 media solution containing 1.6 to 100 µM of 1-benzoyl-3-cyano-pyrrolo[1,2-a]quinoline or other test compound (0.16 to 10 µM final). An aliquot of 45 µL of cells was added to a well of a 96-well microtiter plate containing 5 µL of a 10% DMSO in RPMI-1640 media solution without test compound as the control sample. The samples were mixed by agitation and then incubated at 37° C. for 24 h in a 5% $CO_2$–95% humidity incubator. After incubation, the samples were removed from the incubator and 50 µL of a solution containing 20 µM of N-(Ac-DEVD)-N'-ethoxycarbonyl-R110 fluorogenic substrate (SEQ ID NO:1) (Cytovia, Inc.; U.S. Pat. No. 6,335,429), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model 1420 Wallac Instruments), an initial reading (T=0) was made approximately 1–2 min after addition of the substrate solution, employing excitation at 485 nm and emission at 530 nm, to determine the background fluorescence of the control sample. After approximately 3 h of incubation, the samples were read for fluorescence as above (T=3 h).

Calculation:

The Relative Fluorescence Unit values (RFU) were used to calculate the sample readings as follows:

$RFU_{(T=3h)}$–Control $RFU_{(T=0)}$=Net $RFU_{(T=3h)}$

The activity of caspase cascade activation was determined by the ratio of the net RFU value for 1-benzoyl-3-cyano-pyrrolo[1,2-a]quinoline to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

Caspase Activity and Potency

| The Compound of Example # | T-47D Ratio | T-47D $EC_{50}$ (nM) | ZR-75-1 Ratio | ZR-75-1 $EC_{50}$ (nM) |
|---|---|---|---|---|
| Example A | 7 | 242 | 10 | 243 |
| 1 | 10 | 157 | 7 | 133 |
| 2 | 1 | >10000 | 2 | 5299 |
| 3 | 1 | >10000 | 1 | >10000 |
| 4 | 12 | 463 | 10 | 624 |
| 5 | ND | ND | 11 | 159 |
| 6 | 12 | 2414 | 14 | 1396 |
| 7 | 13 | 351 | 17 | 185 |
| 8 | 12 | 587 | 11 | 2582 |
| 9 | 12 | 150 | 12 | 150 |
| 10 | 6 | 2185 | 14 | 1257 |
| 11 | 17 | 148 | 15 | 147 |
| 12 | 14 | 1163 | 13 | 493 |
| 13 | 1 | >10000 | 2 | 5638 |

Thus, 1-benzoyl-3-cyano-pyrrolo[1,2-a]quinoline (Example A) and other analogs are identified as potent caspase cascade activators and antineoplastic compounds in this assay.

EXAMPLE 85

Identification of 1-Benzoyl-3-cyano-pyrrolo[1,2-a]quinoline as an Antineoplastic Compound that Inhibits Cell Proliferation ($GI_{50}$)

T-47D and SKBr-3 cells were grown and harvested as in Example 84. An aliquot of 90 µL of cells (2.2×10$^4$ cells/mL) was added to a well of a 96-well microtiter plate containing 10 µl of a 10% DMSO in RPMI-1640 media solution containing 1 nM to 100 µM of 1-benzoyl-3-cyano-pyrrolo[1,2-a]quinoline (0.1 nM to 10 µM final). An aliquot of 90 µL of cells was added to a well of a 96-well microtiter plate containing 10 µL of a 10% DMSO in RPMI-1640 media solution without compound as the control sample for maximal cell proliferation ($A_{Max}$). The samples were mixed by agitation and then incubated at 37° C. for 48 h in a 5% $CO_2$–95% humidity incubator. After incubation, the samples were removed from the incubator and 20 µL of CellTiter 96 AQ$_{UEOUS}$ One Solution Cell Proliferation™ reagent (Promega) was added. The samples were mixed by agitation and incubated at 37° C. for 2–4 h in a 5% $CO_2$–95% humidity incubator. Using an absorbance plate reader (Model 1420 Wallac Instruments), an initial reading (T=0) was made approximately 1–2 min after addition of the solution, employing absorbance at 490 nm. This determines the possible background absorbance of the test compounds. No absorbance for 1-benzoyl-3-cyano-pyrrolo[1,2-a]quinoline was found at 490 nm. After the 2–4 h incubation, the samples were read for absorbance as above ($A_{Test}$).

Baseline for $GI_{50}$ (dose for 50% inhibition of cell proliferation) of initial cell numbers were determined by adding an aliquot of 90 µL of cells or 90 µL of media, respectively, to wells of a 96-well microtiter plate containing 10 µL of a 10% DMSO in RPMI-1640 media solution. The samples were mixed by agitation and then incubated at 37° C. for 0.5 h in a 5% $CO_2$–95% humidity incubator. After incubation, the samples were removed from the incubator and 20 µL of CellTiter 96 AQ$_{UEOUS}$ One Solution Cell Proliferation ™ reagent (Promega) was added. The samples were mixed by agitation and incubated at 37° C. for 2–4 h in a 5% $CO_2$–95% humidity incubator. Absorbance was read as above, ($A_{Start}$) defining absorbance for initial cell number used as baseline in $GI_{50}$ determinations.

Calculation:

$GI_{50}$ (dose for 50% inhibition of cell proliferation) is the concentration where $[(A_{Test}-A_{Start})/(A_{Max}-A_{start})]=0.5$.

The $GI_{50}$ (nM) are summarized in Table II:

TABLE II

| The Compound of Example # | $GI_{50}$ in Cancer Cells | |
|---|---|---|
| | $GI_{50}$ (nM) | |
| | T-47D | SKBR-3 |
| Example A | 30 | 32 |
| 1 | 36 | 42 |
| 4 | 138 | 93 |

Thus, 1-benzoyl-3-cyano-pyrrolo[1,2-a]quinoline (Example A) and analogs are identified as antineoplastic compound that inhibits cell proliferation.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

Ar is optionally substituted and is aryl, heteroaryl, saturated carbocyclic, partially saturated carbocyclic, saturated heterocyclic, partially saturated heterocyclic, arylalkyl, or heteroarylalkyl;

$R_1$–$R_8$ are independently hydrogen, halo, haloalkyl, aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido, alkylthiol, alkylsulfonyl or alkylcarboxylate;

the dash line represents either a single bond or a double bond; and

Q is C.

2. The pharmaceutical composition of claim 1, wherein said compound is selected from the group consisting of:

1-Benzoyl-3-cyano-pyrrolo[1,2-α]quinoline;
1-(4-Methyl-benzoyl)-3-(1-oxo-ethyl)-pyrrolo[1,2-a]quinoline;
3-(Ethyl carboxylate)-1-(4-methoxy-benzoyl)-pyrrolo[1,2-a]quinoline;
1-(3-Methoxy-benzoyl)-3-(ethyl carboxylate)-pyrrolo[1,2-a]quinoline;
3-Cyano-1-(3-methoxy-benzoyl)-pyrrolo[1,2-a]quinoline;
1-(3-Bromo-benzoyl)-3-cyano-pyrrolo[1,2-a]quinoline;
3-Cyano-1-(4-methoxy-benzoyl)-pyrrolo[1,2-a]quinoline;
3-Cyano-1-(4-methyl-benzoyl)-pyrrolo[1,2-a]quinoline;

What is claimed is:

1. A pharmaceutical composition comprising a pharmaceutically acceptable carrier and a compound of Formula I:

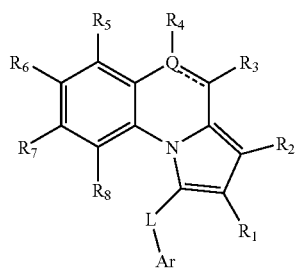

(I)

or a pharmaceutically acceptable salt, wherein:

L is C=O or CHOH;

1-(4-Chloro-benzoyl)-3-cyano-pyrrolo[1,2-a]quinoline;
3-Cyano-1-(4-fluoro-benzoyl)-pyrrolo[1,2-a]quinoline;
1-(4-Bromo-benzoyl)-3-cyano-pyrrolo[1,2-a]quinoline;
1-Benzoyl-3-cyano-7-methyl-pyrrolo[1,2-a]quinoline;
1-Benzoyl-3-cyano-5-methyl-pyrrolo[1,2-a]quinoline;
3-Cyano-1-(4-nitro-benzoyl)-pyrrolo[1,2-a]quinoline;
1-Benzoyl-3-cyano-6,7,8,9-tetrahydro-pyrrolo[1,2-a]quinoline;
3-Cyano-1-(pyridine-2-carbonyl)-pyrrolo[1,2-a]quinoline;
3-Cyano-1-(pyridine-3-carbonyl)-pyrrolo[1,2-a]quinoline;
3-Cyano-1-(4-pyrrolidin-1-yl-benzoyl)-pyrrolo[1,2-a]quinoline;
3-Cyano-1-[hydroxy-(4-methoxyphenyl)-methyl]-pyrrolo[1,2-a]quinoline;
1-(4-Amino-benzoyl)-3-cyano-pyrrolo[1,2-a]quinoline;

3-Cyano-1-(4-imidazol-1-yl-benzoyl)-pyrrolo[1,2-a]quinoline;
3-Cyano-1-cyclopropanecarbonyl-pyrrolo[1,2-a]quinoline;
3-Cyano-1-[4-(methyl carboxylate)benzoyl]-pyrrolo[1,2-a]quinoline;
3-Cyano-1-(4-diethylmino-benzoyl)-pyrrolo[1,2-a]quinoline;
3-Cyano-1-(4-methanesulfonyl-benzoyl)-pyrrolo[1,2-a]quinoline;
3-Cyano-1-[hydroxy-(4-imidazol-1-yl-phenyl)-methyl]-pyrrolo[1,2-a]quinoline;
3-Cyano-1-[imidazol-1-yl-(4-imidazol-1-yl-phenyl)-methyl]-pyrrolo[1,2-a]quinoline;
3-Cyano-1-[4-(4-pyridin-2-yl-piperazin-1-yl)-benzoyl]-pyrrolo[1,2-a]quinoline;
3-Cyano-1-[4-(2-morpholin-4-yl-ethylamino)-benzoyl]-pyrrolo[1,2-a]quinoline;
3-Cyano-1-(4-morpholin-4-yl-benzoyl)-pyrrolo 1,2-a]quinoline;
3-Cyano-1-[4-(4-methyl-piperazin-1-yl)-benzoyl]-pyrrolo[1,2-a]quinoline;
1-Benzoyl-3-cyano-8-methyl-pyrrolo[1,2-a]quinoline;
1-Benzoyl-6-chloro-3-cyano-pyrrolo[1,2-a]quinoline;
1-Benzoyl-4-bromo-3-cyano-pyrrolo[1,2-a]quinoline;
1-Benzoyl-7-chloro-3-cyano-pyrrolo[1,2-a]quinoline;
3-Cyano-1-(morpholine-4-carbonyl)-pyrrolo[1,2-a]quinoline;
3-Cyano-1-(4-pyrazol-1-yl-benzoyl)-pyrrolo[1,2-a]quinoline;
1-Benzoyl-3-cyano-4-methyl-pyrrolo[1,2-a]quinoline;
3-Cyano-1-(4-fluoro-benzoyl)-8-methyl-pyrrolo[1,2-a]quinoline;
3-Cyano-1-(4-imidazol-1-yl-benzoyl)-8-methyl-pyrrolo[1,2-a]quinoline;
3-Cyano-1-(hydroxy-phenyl-methyl)-pyrrolo[1,2-a]quinoline;
3-Cyano-1-[hydroxy-(4-fluorophenyl)-methyl]-pyrrolo[1,2-a]quinoline;
3-Cyano-1-(hydroxy-phenyl-methyl)-8-methyl-pyrrolo[1,2-a]quinoline;
6-Chloro-3-cyano-1-(hydroxy-phenyl-methyl)-pyrrolo[1,2-a]quinoline;
3-Cyano-1-[hydroxy-(4-pyrazol-1-yl-phenyl)-methyl]-pyrrolo[1,2-a]quinoline;
6-Chloro-3-cyano-1-(4-fluoro-benzoyl)-pyrrolo[1,2-a]quinoline;
6-Chloro-3-cyano-1-(4-imidazol-1-yl-benzoyl)-pyrrolo[1,2-a]quinoline;
3-Cyano-1-(4-piperazin-1-yl-benzoyl)-pyrrolo[1,2-a]quinoline;
3-Cyano-1-[4-(3-dimethylamino-propylamino)-benzoyl]-pyrrolo[1,2-a]quinoline;
3-Cyano-1-(3-hydroxy-benzoyl)-pyrrolo[1,2]quinoline;
3-Cyano-1-[3-(2-morpholin-4-yl-ethoxy)benzoyl]-pyrrolo[1,2-a]quinoline;
3-Cyano-1-[3-(2-dimethylamino-ethoxy)benzoyl]-pyrrolo[1,2-a]quinoline;
3-Cyano-1-[3-(carboxymethoxy)benzoyl]-pyrrolo[1,2-a]quinoline;
3-Cyano-1-[3-(2-hydroxyethoxy)benzoyl]-pyrrolo[1,2-a]quinoline;
3-Cyano-1-[2-(dimethylaminomethyl)benzoyl]-pyrrolo[1,2-a]quinoline;
3-Cyano-1-[4-(dimethylaminomethyl)benzoyl]-pyrrolo[1,2-a]quinoline;
3-Cyano-1-[4-(morpholin-4-ylmethyl)benzoyl]-pyrrolo[1,2-a]quinoline;
3-Cyano-1-[4-(4-methylpiperazin-1-ylmethyl)benzoyl]-pyrrolo[1,2-a]quinoline;
3-Cyano-1-[4-(imidazol-1-ylmethyl)benzoyl]-pyrrolo[1,2-a]quinoline;
3-Cyano-1-(4-fluoro-benzoyl)-8-dimethylaminomethyl-pyrrolo[1,2-a]quinoline;
3-Cyano-1-(4-dimethylamino-benzoyl)-pyrrolo[1,2-a]quinoline;
1-Benzoyl-3-cyano-6-nitro-pyrrolo[1,2-a]quinoline;
1-Benzoyl-3-cyano-6-hydroxy-pyrrolo[1,2-a]quinoline;
1-Benzoyl-3-cyano-8-hydroxy-pyrrolo[1,2-α]quinoline;
1-Benzoyl-3-cyano-6-(2-morpholin-4-yl-ethoxy)-pyrrolo[1,2-a]quinoline;
1-Benzoyl-3-cyano-6-(2-dimethylamino-ethoxy)-pyrrolo[1,2-a]quinoline;
1-Benzoyl-3-cyano-8-(2-morpholin-4-yl-ethoxy)-pyrrolo[1,2-a]quinoline;
1-Benzoyl-3-cyano-8-(2-dimethylamino-ethoxy)-pyrrolo[1,2-a]quinoline;
1-(3-Methoxy-benzoyl)-pyrrolo[1,2-a]quinoline-3-carboxylic acid;
1-(3-Methoxy-benzoyl)-pyrrolo[1,2-a]quinoline-3-carboxylic acid N-hydroxysuccinimidyl ester;
1-(3-Methoxy-benzoyl)-pyrrolo[1,2-a]quinoline-3-carboxylic acid (2-hydroxy-ethyl)-amide;
1-(3-Methoxy-benzoyl)-pyrrolo[1,2-a]quinoline-3-carboxylic acid (2-morpholin-4-yl-ethyl)-amide;
1-(3-Methoxy-benzoyl)-pyrrolo[1,2-a]quinoline-3-carboxylic acid hydroxy-amide;
1-(3-Methoxy-benzoyl)-pyrrolo[1,2-a]quinoline-3-carboxylic acid (2-amino-ethyl)-amide;
1-(3-Methoxy-benzoyl)-pyrrolo[1,2-a]quinoline-3-carboxylic acid (3-dimethylamino-propyl)-amide;
1-(3-Methoxy-benzoyl)-pyrrolo[1,2-a]quinoline-3-carboxylic acid {2-[2-(2-amino-ethoxy)-ethoxy-]-ethyl}-amide;
1-(3-Methoxy-benzoyl)-3-(4-methyl-piperazine-1-carbonyl)-pyrrolo[1,2-a]quinoline;
1-(3-Methoxy-benzoyl)-pyrrolo[1,2-a]quinoline-3-carboxylic acid (2-piperazin-1-yl-ethyl)-amide;
3-Cyano-1-(2-fluoro-benzoyl)-pyrrolo[1,2-a]quinoline;
3-Cyano-1-(2-methylbenzoyl)-pyrrolo [1,2-a]quinoline;
3-Cyano-1-(4-acetamido-3-nitro-benzoyl)-pyrrolo [1,2-a]quinoline;
3-Cyano-1-(2-imidazol-1-yl-benzoyl)-pyrrolo[1,2-a]quinoline;
3-Cyano-1-(2-morpholine-1-yl-benzoyl)-pyrrolo[1,2-a]quinoline; and
3-Cyano-1-(4-carboxy-benzoyl)-pyrrolo[1,2-a]quinoline;
or a pharmaceutically acceptable salt or thereof.

3. A compound of Formula I:

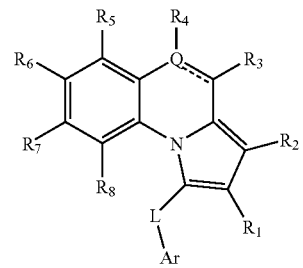

(I)

or a pharmaceutically acceptable salt or thereof, wherein:
L is C=O or CHOH;

Ar is optionally substituted and is aryl, heteroaryl, saturated carbocyclic, partially saturated carbocyclic, saturated heterocyclic, partially saturated heterocyclic, arylalkyl, or heteroarylalkyl;

$R_1$–$R_8$ are independently hydrogen, halo, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol or alkylsulfonyl;

the dash line represents either a single bond or a double bond; and

Q is C with the proviso that when $R_2$ is CN, L is C=O and Ar is phenyl then at least one of the $R_1$ and $R_3$–$R_8$ is other than hydrogen.

4. The compound of claim 3, wherein L is C=O.

5. The compound of claim 3, wherein the dash line is a double bond.

6. The compound of claim 3, wherein R2 is CN.

7. The compound of claim 3, wherein Ar is phenyl, naphthyl, pyridyl, quinolyl, isoquinolyl, thienyl, furyl, pyrrolyl, indolyl, or cyclohexyl, each of which is optionally substituted.

8. The compound of claim 7, wherein Ar is optionally substituted and is phenyl or pyridyl.

9. The compound of claim 3, wherein $R_1$–$R_8$ are independently hydrogen, halo, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol, or alkylsulfonyl.

10. The compound of Formula II:

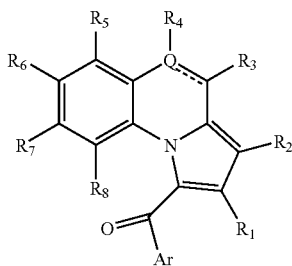

(II)

or a pharmaceutically acceptable salt thereof, wherein:

Ar is optionally substituted and is aryl, heteroaryl, saturated carbocyclic, partially saturated carbocyclic, saturated heterocyclic, partially saturated heterocyclic, arylalkyl, or heteroarylalkyl;

$R_1$–$R_8$ are independently hydrogen, halo, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol or alkylsulfonyl;

the dash line represents either a single bond or a double bond; and

Q is C, with the proviso that when $R_2$ is CN and Ar is phenyl, then at least one of the $R_1$ and $R_3$–$R_8$ is other than hydrogen.

11. The compound of claim 10, wherein Q is C and the dash line is a double bond.

12. The compound of claim 10, wherein R2 is CN.

13. The compound of claim 10, wherein Ar is phenyl, naphthyl, pyridyl, quinolyl, isoquinolyl, thienyl, furyl, pyrrolyl, indolyl, or cyclohexyl, each of which is optionally substituted.

14. The compound of claim 13, wherein Ar is optionally substituted and is phenyl or pyridyl.

15. A compound of Formula III:

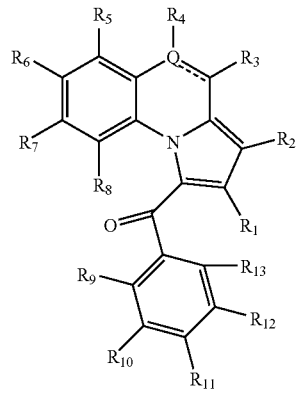

(III)

or a pharmaceutically acceptable salt thereof, wherein:

$R_1$–$R_8$ are independently hydrogen, halo, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocyclealkyl, heterocyclealkyl, hydroxyalkyl, nitro, amino, cyano, acylamido, hydroxy, thiol, acyloxy, azido, alkoxy, carboxy, carbonylamido, alkylthiol or alkylsulfonyl;

$R_9$–$R_{13}$ are independently hydrogen, halo, $C_1$–$C_6$ haloalkyl, $C_6$–$C_{10}$ aryl, heteroaryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy, carboxy, ($C_1$–$C_6$)alkylsulfonyl or ($C_1$–$C_6$)alkylcarboxylate;

the dash line represents either a single bond or a double bond; and

Q is C;

with the proviso that when $R_2$ is CN, then at least one of the $R_1$ and $R_3$–$R_{13}$ is other than hydrogen.

16. The compound of claim 15, wherein the dash line is a double bond.

17. The compound of claim 15, wherein R2 is CN.

18. The compound of claim 15, wherein $R_1$–$R_8$ are independently hydrogen, halo, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido, alkylthiol or alkylsulfonyl.

19. A compound selected from the group consisting of:

3-Cyano-1-(3-methoxy-benzoyl)-pyrrolo[1,2-a]quinoline;

1-(3-Bromo-benzoyl)-3-cyano-pyrrolo[1,2-a]quinoline;

3-Cyano-1-(4-methoxy-benzoyl)-pyrrolo[1,2-a]quinoline;

3-Cyano-1-(4-methyl-benzoyl)-pyrrolo[1,2-a]quinoline;

1-(4-Chloro-benzoyl)-3-cyano-pyrrolo[1,2-a]quinoline;
3-Cyano-1-(4-fluoro-benzoyl)-pyrrolo[1,2-a]quinoline;
1-(4-Bromo-benzoyl)-3-cyano-pyrrolo[1,2-a]quinoline;
1-Benzoyl-3-cyano-7-methyl-pyrrolo[1,2-a]quinoline;
1-Benzoyl-3-cyano-5-methyl-pyrrolo[1,2-a]quinoline;
3-Cyano-1-(4-nitro-benzoyl)-pyrrolo[1,2-a]quinoline;
1-Benzoyl-3-cyano-6,7,8,9-tetrahydro-pyrrolo[1,2-a]quinoline;
3-Cyano-1-(pyridine-2-carbonyl)-pyrrolo[1,2-a]quinoline;
3-Cyano-1-(pyridine-3-carbonyl)-pyrrolo[1,2-a]quinoline;
3-Cyano-1-(4-pyrrolidin-1-yl-benzoyl)-pyrrolo[1,2-a]quinoline;
3-Cyano-1-[hydroxy-(4-methoxyphenyl)-methyl]-pyrrolo[1,2-a]quinoline;
1-(4-Amino-benzoyl)-3-cyano-pyrrolo[1,2-a]quinoline;
3-Cyano-1-(4-imidazol-1-yl-benzoyl)-pyrrolo[1,2-a]quinoline;
3-Cyano-1-cyclopropanecarbonyl-pyrrolo[1,2-a]quinoline;
3-Cyano-1-[4-(methyl carboxylate)benzoyl]-pyrrolo[1,2-a]quinoline;
3-Cyano-1-(4-diethylmino-benzoyl)-pyrrolo[1,2-a]quinoline;
3-Cyano-1-(4-methanesulfonyl-benzoyl)-pyrrolo[1,2-a]quinoline;
3-Cyano-1-[hydroxy-(4-imidazol-1-yl-phenyl)-methyl]-pyrrolo[1,2-a]quinoline;
3-Cyano-1-[imidazol-1-yl-(4-imidazol-1-yl-phenyl)-methyl]-pyrrolo[1,2-a]quinoline;
3-Cyano-1-[4-(4-pyridin-2-yl-piperazin-1-yl)-benzoyl]-pyrrolo[1,2-a]quinoline;
3-Cyano-1-[4-(2-morpholin-4-yl-ethylamino)-benzoyl]-pyrrolo[1,2-a]quinoline;
3-Cyano-1-(4-morpholin-4-yl-benzoyl)-pyrrolo[1,2-a]quinoline;
3-Cyano-1-[4-(4-methyl-piperazin-1-yl)-benzoyl]-pyrrolo[1,2-a]quinoline;
1-Benzoyl-3-cyano-8-methyl-pyrrolo[1,2-a]quinoline;
1-Benzoyl-6-chloro-3-cyano-pyrrolo[1,2-a]quinoline;
1-Benzoyl-4-bromo-3-cyano-pyrrolo[1,2-a]quinoline;
1-Benzoyl-7-chloro-3-cyano-pyrrolo[1,2-a]quinoline;
3-Cyano-1-(morpholine-4-carbonyl)-pyrrolo[1,2-a]quinoline;
3-Cyano-1-(4-pyrazol-1-yl-benzoyl)-pyrrolo[1,2-a]quinoline;
1-Benzoyl-3-cyano-4-methyl-pyrrolo[1,2-a]quinoline;
3-Cyano-1-(4-fluoro-benzoyl)-8-methyl-pyrrolo[1,2-a]quinoline;
3-Cyano-1-(4-imidazol-1-yl-benzoyl)-8-methyl-pyrrolo[1,2-a]quinoline;
3-Cyano-1-(hydroxy-phenyl-methyl)-pyrrolo[1,2-a]quinoline;
3-Cyano-1-[hydroxy-(4-fluorophenyl)-methyl]-pyrrolo[1,2-a]quinoline;
3-Cyano-1-(hydroxy-phenyl-methyl)-8-methyl-pyrrolo[1,2-a]quinoline;
6-Chloro-3-cyano-1-(hydroxy-phenyl-methyl)-pyrrolo[1,2-a]quinoline;
3-Cyano-1-[hydroxy-(4-pyrazol-1-yl-phenyl)-methyl]-pyrrolo[1,2-a]quinoline;
6-Chloro-3-cyano-1-(4-fluoro-benzoyl)-pyrrolo[1,2-a]quinoline;
6-Chloro-3-cyano-1-(4-imidazol-1-yl-benzoyl)-pyrrolo[1,2-a]quinoline;
3-Cyano-1-(4-piperazin-1-yl-benzoyl)-pyrrolo[1,2-a]quinoline;
3-Cyano-1-[4-(3-dimethylamino-propylamino)-benzoyl]-pyrrolo[1,2-a]quinoline;
3-Cyano-1-(3-hydroxy-benzoyl)-pyrrolo[1,2-a]quinoline;
3-Cyano-1-[3-(2-morpholin-4-yl-ethoxy)benzoyl]-pyrrolo[1,2-a]quinoline;
3-Cyano-1-[3-(2-dimethylamino-ethoxy)benzoyl]-pyrrolo[1,2-a]quinoline;
3-Cyano-1-[3-(carboxymethoxy)benzoyl]-pyrrolo[1,2-a]quinoline;
3-Cyano-1-[3-(2-hydroxyethoxy)benzoyl]-pyrrolo[1,2-a]quinoline;
3-Cyano-1-[2-(dimethylaminomethyl)benzoyl]-pyrrolo[1,2-a]quinoline;
3-Cyano-1-[4-(dimethylaminomethyl)benzoyl]-pyrrolo[1,2-a]quinoline;
3-Cyano-1-[4-(morpholin-4-ylmethyl)benzoyl]-pyrrolo[1,2-a]quinoline;
3-Cyano-1-[4-(4-methylpiperazin-1-ylmethyl)benzoyl]-pyrrolo[1,2-a]quinoline;
3-Cyano-1-[4-(imidazol-1-ylmethyl)benzoyl]-pyrrolo[1,2-a]quinoline;
3-Cyano-1-(4-fluoro-benzoyl)-8-dimethylaminomethyl-pyrrolo[1,2-a]quinoline;
3-Cyano-1-(4-dimethylamino-benzoyl)-pyrrolo[1,2-a]quinoline;
1-Benzoyl-3-cyano-6-nitro-pyrrolo[1,2-a]quinoline;
1-Benzoyl-3-cyano-6-hydroxy-pyrrolo[1,2-a]quinoline;
1-Benzoyl-3-cyano-8-hydroxy-pyrrolo[1,2-a]quinoline;
1-Benzoyl-3-cyano-6-(2-morpholin-4-yl-ethoxy)-pyrrolo[1,2-a]quinoline;
1-Benzoyl-3-cyano-6-(2-dimethylamino-ethoxy)-pyrrolo[1,2-a]quinoline;
1-Benzoyl-3-cyano-8-(2-morpholin-4-yl-ethoxy)-pyrrolo[1,2-a]quinoline;
1-Benzoyl-3-cyano-8-(2-dimethylamino-ethoxy)-pyrrolo[1,2-a]quinoline;
1-(3-Methoxy-benzoyl)-pyrrolo[1,2-a]quinoline-3-carboxylic acid;
1-(3-Methoxy-benzoyl)-pyrrolo[1,2-a]quinoline-3-carboxylic acid N-hydroxysuccinimidyl ester;
1-(3-Methoxy-benzoyl)-pyrrolo[1,2-a]quinoline-3-carboxylic acid (2-hydroxy-ethyl)-amide;
1-(3-Methoxy-benzoyl)-pyrrolo[1,2-a]quinoline-3-carboxylic acid (2-morpholin-4-yl-ethyl)-amide;
1-(3-Methoxy-benzoyl)-pyrrolo[1,2-a]quinoline-3-carboxylic acid hydroxy-amide;
1-(3-Methoxy-benzoyl)-pyrrolo[1,2-a]quinoline-3-carboxylic acid (2-amino-ethyl)-amide;
1-(3-Methoxy-benzoyl)-pyrrolo[1,2-a]quinoline-3-carboxylic acid (3-dimethylamino-propyl)-amide;
1-(3-Methoxy-benzoyl)-pyrrolo[1,2-a]quinoline-3-carboxylic acid {2-[2-(2-amino-ethoxy)-ethoxy-]-ethyl}-amide;
1-(3-Methoxy-benzoyl)-3-(4-methyl-piperazine-1-carbonyl)-pyrrolo[1,2-a]quinoline;
1-(3-Methoxy-benzoyl)-pyrrolo[1,2-a]quinoline-3-carboxylic acid (2-piperazin-1-yl-ethyl)-amide;
3-Cyano-1-(2-fluoro-benzoyl)-pyrrolo[1,2-a]quinoline;
3-Cyano-1-(2-methylbenzoyl)-pyrrolo[1,2-a]quinoline;
3-Cyano-1-(4-acetamido-3-nitro-benzoyl)-pyrrolo[1,2-a]quinoline;
3-Cyano-1-(2-imidazol-1-yl-benzoyl)-pyrrolo[1,2-a]quinoline;
3-Cyano-1-(2-morpholine-1-yl-benzoyl)-pyrrolo[1,2-a]quinoline; and
3-Cyano-1-(4-carboxy-benzoyl)-pyrrolo[1,2-a]quinoline;
or a pharmaceutically acceptable salt thereof.

20. A method of treating cancer comprising administering to an animal in need of such treatment an effective amount of a compound of Formula I:

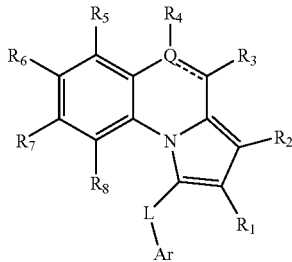
(I)

or a pharmaceutically acceptable salt thereof, wherein:
L is C=O or CHOH;
Ar is optionally substituted and is aryl, heteroaryl, saturated carbocyclic, partially saturated carbocyclic, saturated heterocyclic, partially saturated heterocyclic, arylalkyl or heteroarylalkyl;

$R_1$–$R_8$ are independently hydrogen, halo, haloalkyl, aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido, alkylthiol, alkylsulfonyl or alkylcarboxylate;

the dash line represents either a single bond or a double bond; and

Q is C, wherein said cancer is selected from the group consisting of colon cancer, lymphoma cancer, prostate cancer, lung cancer and breast cancer.

21. The method of claim 20, wherein said cancer is lung cancer.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: N-blocked tetrapeptide substrate of a caspase

<400> SEQUENCE: 1

Asp Glu Val Asp
1
```